US010016381B2

(12) United States Patent
Naccari et al.

(10) Patent No.: US 10,016,381 B2
(45) Date of Patent: **\*Jul. 10, 2018**

(54) COMPOUNDS AND THEIR SALTS SPECIFIC TO THE PPAR RECEPTORS AND THE EGF RECEPTORS AND THEIR USE IN THE MEDICAL FIELD

(71) Applicant: Nogra Pharma Limited, Dublin (IE)

(72) Inventors: Giancarlo Naccari, Monza (IT); Sergio Baroni, Villa d'adda (IT)

(73) Assignee: Nogra Pharma Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/377,013

(22) Filed: Dec. 13, 2016

(65) Prior Publication Data

US 2017/0312239 A1 Nov. 2, 2017

Related U.S. Application Data

(60) Continuation of application No. 14/671,579, filed on Mar. 27, 2015, now Pat. No. 9,561,202, which is a
(Continued)

(30) Foreign Application Priority Data

Jul. 22, 2005 (IT) .............................. RM2005A0389

(51) Int. Cl.
*A61K 31/196* (2006.01)
*C07C 229/42* (2006.01)

(52) U.S. Cl.
CPC .......... *A61K 31/196* (2013.01); *C07C 229/42* (2013.01)

(58) Field of Classification Search
None
See application file for complete search history.

(56) References Cited

U.S. PATENT DOCUMENTS 3,211,610 A 10/1965 Rogers
3,444,232 A 5/1969 Bernstein
(Continued)

FOREIGN PATENT DOCUMENTS

EP 0055689 A1 7/1982
EP 0102833 A1 3/1984
(Continued)

OTHER PUBLICATIONS

Ahnfelt-Ronne et al. (1990) "Clinical Evidence Supporting the Radical Scavenger Mechanism of 5-Aminosalicylic Acid", Gastroenterology, 98(5 Pt 1):1162-9.
(Continued)

*Primary Examiner* — Karl J Puttlitz
(74) *Attorney, Agent, or Firm* — Goodwin Procter LLP

(57) ABSTRACT

The present invention relates to compounds comprising the general formula (I), in which $R_1$ and $R_2$, which may be identical or different, are selected from the group comprising —H or a linear or branched alkyl group having from 1 to 6 carbon atoms or together form an aromatic or aliphatic ring with 5 or 6 atoms; Y and Z, which may be identical or different, are selected from the group comprising —H, —OH, —COOH, —OR$_3$, —CH(OR$_3$)COOH, in which $R_3$ is selected from H, phenyl, benzyl, —CF$_3$ or —CF$_2$CF$_3$, vinyl, allyl and a linear or branched alkyl group having from 1 to 6 carbon atoms.

12 Claims, 13 Drawing Sheets

Figure 1:
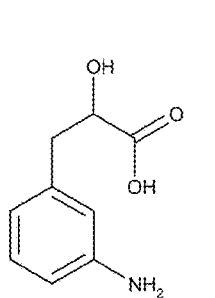
Figure 1:
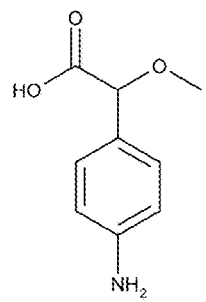
Figure 1:
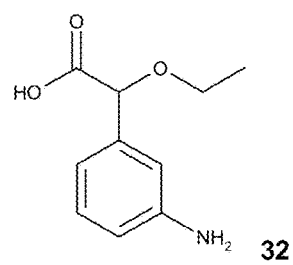
Figure 1:
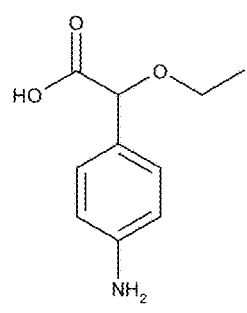
Figure 1:
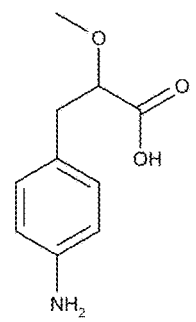
Figure 1:
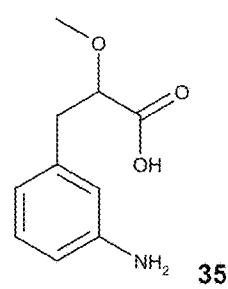
Figure 1:
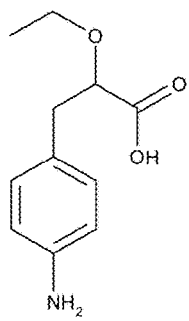
Figure 1:
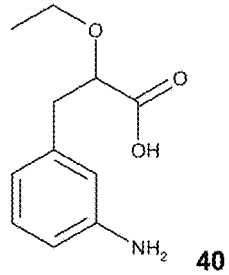

Structure of compounds 20, 23, 32, 33, 34, 35, 39, 40

Related U.S. Application Data division of application No. 14/202,386, filed on Mar. 10, 2014, now Pat. No. 9,133,099, which is a continuation of application No. 13/408,439, filed on Feb. 29, 2012, now Pat. No. 8,710,100, which is a division of application No. 11/989,090, filed as application No. PCT/IE2006/000078 on Jul. 24, 2006, now Pat. No. 8,153,841.

(56)  References Cited

U.S. PATENT DOCUMENTS

| | | |
|---|---|---|
| 4,036,951 A | 7/1977 | Halpern et al. |
| 4,348,223 A | 9/1982 | Grove |
| 4,404,215 A | 9/1983 | Vincent et al. |
| 4,429,152 A | 1/1984 | Gries et al. |
| 4,720,506 A | 1/1988 | Munakata et al. |
| 4,869,913 A | 9/1989 | Gries et al. |
| 4,933,330 A | 6/1990 | Jorgensen et al. |
| 5,262,549 A | 11/1993 | Telfer et al. |
| 5,302,751 A | 4/1994 | Manimaran et al. |
| 5,519,014 A | 5/1996 | Borody |
| 5,594,015 A | 1/1997 | Kurtz et al. |
| 5,594,151 A | 1/1997 | Stolowitz |
| 6,114,382 A | 9/2000 | Moretti |
| 6,194,627 B1 | 2/2001 | Geissler et al. |
| 6,326,364 B1 | 12/2001 | Lin et al. |
| 6,403,656 B1 | 6/2002 | Rivier et al. |
| 6,583,128 B2 | 6/2003 | Ekwuribe et al. |
| 6,602,869 B1 | 8/2003 | Galey et al. |
| 6,844,003 B2 | 1/2005 | Galey et al. |
| 6,884,821 B1 | 4/2005 | Shinoda et al. |
| 6,903,082 B2 | 6/2005 | Ekwuribe et al. |
| 7,049,342 B2 | 5/2006 | Miyachi et al. |
| 7,098,025 B1 | 8/2006 | Auwerx et al. |
| 7,176,204 B2 | 2/2007 | Miyachi et al. |
| 7,425,578 B2 | 9/2008 | Ekwuribe et al. |
| 7,429,676 B2 | 9/2008 | Woltering et al. |
| 7,749,980 B2 | 7/2010 | Plourde, Jr. et al. |
| 7,998,474 B2 | 8/2011 | Kelly |
| 8,030,520 B2 | 10/2011 | Sundermeier et al. |
| 8,138,357 B2 | 3/2012 | Naccari et al. |
| 8,153,693 B2 | 4/2012 | Baroni et al. |
| 8,153,841 B2 | 4/2012 | Naccari et al. |
| 8,450,506 B2 | 5/2013 | Naccari et al. |
| 8,501,806 B2 | 8/2013 | Baroni et al. |
| 8,710,100 B2 | 4/2014 | Naccari et al. |
| 8,754,127 B2 | 6/2014 | Baroni et al. |
| 8,796,334 B2 | 8/2014 | Baroni et al. |
| 9,133,099 B2 | 9/2015 | Naccari et al. |
| 9,345,680 B2 | 5/2016 | Naccari et al. |
| 9,511,041 B2 | 12/2016 | Baroni et al. |
| 9,561,202 B2 | 2/2017 | Naccari et al. |
| 9,682,050 B2 | 6/2017 | Baroni et al. |
| 9,682,923 B2 | 6/2017 | Baroni et al. |
| 2003/0113815 A1 | 6/2003 | Houseknecht et al. |
| 2003/0133875 A1 | 7/2003 | Kelly |
| 2003/0220374 A1 | 11/2003 | Needleman |
| 2003/0229083 A1 | 12/2003 | Debnath et al. |
| 2004/0034067 A1 | 2/2004 | MacPhee |
| 2004/0115127 A1 | 6/2004 | Wright et al. |
| 2004/0132110 A1 | 7/2004 | Desreumaux et al. |
| 2006/0159648 A1 | 7/2006 | Davis et al. |
| 2006/0177444 A1 | 8/2006 | Horizoe |
| 2006/0270635 A1 | 11/2006 | Wallace et al. |
| 2007/0086967 A1 | 4/2007 | MacDonald |
| 2007/0149804 A1 | 6/2007 | Woltering et al. |
| 2009/0048343 A1 | 2/2009 | Naccari et al. |
| 2009/0118357 A1 | 5/2009 | Naccari et al. |
| 2010/0305077 A1 | 12/2010 | Baroni et al. |
| 2011/0105748 A1 | 5/2011 | Bhuniya et al. |
| 2011/0152225 A1 | 6/2011 | Baroni et al. |
| 2011/0288058 A1 | 11/2011 | Baroni et al. |
| 2011/0288177 A1 | 11/2011 | Baroni et al. |
| 2012/0053244 A1 | 3/2012 | Baroni et al. |
| 2012/0053245 A1 | 3/2012 | Baroni et al. |
| 2012/0157417 A1 | 6/2012 | Baroni et al. |
| 2012/0316230 A1 | 12/2012 | Naccari et al. |
| 2013/0005813 A1 | 1/2013 | Naccari et al. |
| 2015/0045436 A1 | 2/2015 | Naccari et al. |
| 2015/0051285 A1 | 2/2015 | Baroni et al. |
| 2015/0087678 A1 | 3/2015 | Baroni et al. |
| 2015/0087708 A1 | 3/2015 | Baroni et al. |
| 2015/0148418 A1 | 5/2015 | Baroni et al. |
| 2015/0250749 A1 | 9/2015 | Giuliani et al. |
| 2015/0265514 A1 | 9/2015 | Giuliani et al. |
| 2015/0265562 A1 | 9/2015 | Naccari et al. |
| 2015/0265563 A1 | 9/2015 | Naccari et al. |
| 2016/0338927 A1 | 11/2016 | Baroni et al. |
| 2017/0056349 A1 | 3/2017 | Baroni et al. |
| 2017/0172956 A1 | 6/2017 | Baroni et al. |

FOREIGN PATENT DOCUMENTS

| | | |
|---|---|---|
| EP | 0279096 A2 | 8/1988 |
| EP | 0291159 A2 | 11/1988 |
| EP | 0352826 A2 | 1/1990 |
| EP | 0623104 B1 | 8/1997 |
| EP | 0938459 B1 | 7/2002 |
| EP | 1285908 A1 | 2/2003 |
| EP | 1348698 A1 | 10/2003 |
| EP | 0554291 B1 | 12/2003 |
| EP | 1607103 A1 | 12/2005 |
| EP | 1274407 B1 | 3/2006 |
| EP | 1801093 B1 | 3/2009 |
| EP | 1448995 B1 | 1/2011 |
| EP | 2298321 A1 | 3/2011 |
| EP | 2107047 B1 | 9/2011 |
| GB | 767788 A | 2/1957 |
| GB | 1359560 | 7/1974 |
| JP | 2003-516310 A | 5/2003 |
| JP | 3425441 B2 | 7/2003 |
| JP | 3435651 B2 | 8/2003 |
| JP | 2004-528329 A | 9/2004 |
| JP | 2005-510733 A | 4/2005 |
| JP | 2009-242399 A | 10/2009 |
| WO | WO-1992/006690 A1 | 4/1992 |
| WO | WO-1993/014056 A1 | 7/1993 |
| WO | WO-1994/000135 A1 | 1/1994 |
| WO | WO-1995/031194 A1 | 11/1995 |
| WO | WO-1996/030016 A2 | 10/1996 |
| WO | WO-1997/025042 A1 | 7/1997 |
| WO | WO-1998/006387 A2 | 2/1998 |
| WO | WO-1998/043081 A1 | 10/1998 |
| WO | WO-1999/015520 A1 | 4/1999 |
| WO | WO-2000/059866 A1 | 10/2000 |
| WO | WO-2000/062766 A2 | 10/2000 |
| WO | WO-2001/002388 A1 | 1/2001 |
| WO | WO-2001/025181 A1 | 4/2001 |
| WO | WO-2001/079153 A1 | 10/2001 |
| WO | WO-2002/046161 A1 | 6/2002 |
| WO | WO-2002/077651 A1 | 10/2002 |
| WO | WO-2002/085123 A1 | 10/2002 |
| WO | WO-2002/095393 A2 | 11/2002 |
| WO | WO-2003/046580 A1 | 6/2003 |
| WO | WO-2003/048116 A2 | 6/2003 |
| WO | WO-2004/073622 A2 | 9/2004 |
| WO | WO-2005/012280 A1 | 2/2005 |
| WO | WO-2005/040102 A2 | 5/2005 |
| WO | WO-2005/072113 A2 | 8/2005 |
| WO | WO-2005/084658 A1 | 9/2005 |
| WO | WO-2006/072175 A1 | 7/2006 |
| WO | WO-2007/010514 A2 | 1/2007 |
| WO | WO-2007/010516 A2 | 1/2007 |
| WO | WO-2007/096148 A1 | 8/2007 |
| WO | WO-2008/094618 A2 | 8/2008 |
| WO | WO-2008/104557 A1 | 9/2008 |
| WO | WO-2009/025854 A1 | 2/2009 |
| WO | WO-2009/080828 A2 | 7/2009 |
| WO | WO-2010/063470 A2 | 6/2010 |
| WO | WO-2010/063472 A2 | 6/2010 |
| WO | WO-2010/091892 A2 | 8/2010 |
| WO | WO-2010/091894 A2 | 8/2010 |
| WO | WO-2013/012662 A2 | 1/2013 |
| WO | WO-2013/064153 A1 | 5/2013 |

(56) References Cited

FOREIGN PATENT DOCUMENTS

| WO | WO-2013/117744 A9 | 8/2013 |
|---|---|---|
| WO | WO-2013/156413 A1 | 10/2013 |
| WO | WO-2013/178815 A1 | 12/2013 |
| WO | WO-2013/178816 A1 | 12/2013 |
| WO | WO-2014/041140 A1 | 3/2014 |
| WO | WO-2014/041141 A1 | 3/2014 |
| WO | WO-2016/154730 A1 | 10/2016 |
| WO | WO-2016/202341 A1 | 12/2016 |

OTHER PUBLICATIONS

Allgayer (2003) "Review Article: Mechanisms of Action of Mesalazine in Preventing Colorectal Carcinoma in Inflammatory Bowel Disease," Aliment Pharmacol Ther, 18(Suppl. 2):10-4.
Ameho et al., (1997) 'Prophylactic Effect of Dietary Glutamine Supplementation on Interleukin 8 and Tumor Necrosis Factor Alpha Production in Trinitrobenzene Sulphonic Acid Induced Colitis,' Gut, 41(4):487-93.
Australian Examination Report dated Jan. 31, 2014, for Application No. 2009321722 (9 pages).
Azhar, (2010), 'Peroxisome Proliferator-Activated Receptors, Metabolic Syndrome and Cardiovascular Disease,' Future Cardiol, 6(5):657-91 (NIH Public Access Author Manuscript).
Baker et al., (1962) "Potential Anticancer Agents. LXXVIII Non-classical Antimetabolites. IV. Synthesis of Compounds Related to 4-(Iodoacetamido) Salicylie Acid, an Exo-Alkylating Irreversible Inhibitor," J Org Chem, 27(9):3283-95.
Baz et al. (2003) 'Oxidant / Antioxidant Status in Patients with Psoriasis,' Yonsei Med J, 44(6):987-90.
Behshad et al., (2008) 'A Retrospective Case Series Review of the Peroxisome Proliferator-Activated Receptor Ligand Rosiglitazone in the Treatment of Atopic Dermatitis,' Arch Dermatol, 144(1):84-8.
Beilstein Database Beistein Institute zur Forderung der Chemischen Wissenschaften, Frankfurt an Main, DE XP002413839, Accession No. 2092096, J. Med. Chem., 22: 589 (1979).
Beilstein Database, Beilstein Institute for Organic Chemistry, Frankfurt an Main, DE, retrieved from XFIRE, Accession No. brn 2208094, J. Am. Chem. Soc., 68: 2335, 2338 (1946).
Beilstein Database, Beilstein Institute for Organic Chemistry, Frankfurt an Main, DE, retrieved from XFIRE, Accession No. brn 2803076, J. Org. Chem., 14: 1013, 1018 (1949).
Beilstein Database, Beilstein Institute for Organic Chemistry, Frankfurt an Main, DE, retrieved from XFIRE, Accession No. brn 3199913, Chem. Ber., 46: 3978 (1913).
Beilstein Database, Beilstein Institute for Organic Chemistry, Frankfurt an Main, DE, retrieved from XFIRE, Accession No. brn 3200601, J. Chem. Soc., pp. 104, 111 (1935).
Beilstein Database, Beilstein Institute for Organic Chemistry, Frankfurt an Main, DE, retrieved from XFIRE, Accession No. brn 3268495, Justus Liebigs Ann. Chem., 463:60 (1924).
Beilstein Database, Beilstein Institute for Organic Chemistry, Frankfurt an Main, DE, retrieved from XFIRE, Accession No. brn 3296969, Chem. News J. Ind. Sci, 36: 269 (1877).
Beilstein Database, Beilstein Institute for Organic Chemistry, Frankfurt an Main, DE, retrieved from XFIRE, Accession No. pcrn 859019, U.S. Pat. No. 4,429,152 A (Jan. 1984).
Beilstein Database, Beilstein Institute for Organic Chemistsry, Frankfurt an Main, DE, retrieved from XFIRE, Accession No. brn 3199917, Chem. Ber., 46: 288 (1913).
Beilstein Database, Beilstsein Institute for Organic Chemistry, Frankfurt an Main, DE, retrieved from XFIRE, Accession No. brn 3242057, Chem. Ber., 74:500, 517 (1941).
Beilstein Database, Beistein Institut zur Forderung der Chemischen Wissenschaften, Frankfurt an Main, DE, XP002413837, Accession No. 2367395, Chem. Ber., 87: 179-181 (1954.).
Beilstein Database, Beistein Institut zur Forderung der Chemischen Wissenschaften, Frankfurt an Main, DE, XP002413838, Accession No. 2839685, J. Am. Chem Soc., 73: 903-904 (1951).
Beilstein Database, Beistein Institut zur Forderung der Chemischen Wissenschaften, Frankfurt an Main, DE, XP002413840, Accession No. 3031462, Bull Soc. Chim Belg., 61: 310-320 (1952).
Beilstein Database, Beistein Institut zur Forderung der Chemischen Wissenschaften, Frankfurt an Main, DE, XP002413842, Accession No. 3259704, Justus Liebigs Ann Chem, 429: 173 (1922).
Beilstein Database, Beistein Institut zur Förderrung der Chemischen Wisssenschaften, Frankfurt an Main, DE, XP002413836, Accession No. 1869425, J. Labelled Compd Radiopharm, 44: S225-S227 (2001).
Beilstein Database, Beisten Insstitut zur Forderung der Chemischen Wissenschaften, Frankfurt an Main, DE, XP002413843, Accession No. 3530419, Justus Liebigs Ann Chem, 429: 164 (1922).
Beilstein Database, Beisten Institut zur Forderung der Chemischen Wissenschaften, Frankfurt an Main, DE, XP002413841, Accession No. 2641495, J. Org. Chem., 27: 3283-3295 (1962).
Bickers et al., (2006) 'Oxidative Stress in the Pathogenesis of Skin Disease,' J Invest Dermatol, 126(2)2565-75.
Bongartz et al., (2005) 'Treatment of Active Psoriatic Arthritis with the PPARγ Ligand Pioglitazone: An Open-Label Pilot Study,' Rheumatology, 44(1):126-9.
Broadwith (2009) "Enzyme Binds Both Sides of the Mirror," Chem World, Nov. 6, 2009, https://www.chemistryworld.com/news/enzyme-binds-both-sides-of-the-mirror/1016647.article (2 pages).
Brown and Joyeau, (1979), 'Use of p-Aminophenyl D and L-Lactic Acids and p-Aminophenyl Pyruvic Acid as Effectors in the Affinity Chromatography of Lactate Dehydrogenase,' Biochimie, 61(3):437-42 (Abstract only).
Brown et al., (1978) "Chimie Organique," C.R. Acad. Sc. Paris, t. 287:125-8.
Brunton et al., (1997) "A Role of Epidermal Growth Factor Receptor, c-Src and Focal Adhesion Kinase in an in vitro Model for the Progression of Colon Cancer," Oncogene, 14( 3):283-93.
Bull (2003) "The Role of Peroxisome Proliferator-Activated Receptor γ in Colon Cancer and Inflammatory Bowel Disease," Arch Pathol Lab Med, 127(9):1121-3.
Casen Recordati Group, (2016), 'Cleen Ready-to-Use Enema, Summary of Product Characteristics Updated Jun. 16, 2016,' emc+, medicines.org.Uk/emc, XP-002763390, <https://www.medicines.org.UK/emc/print-document?documentId=542> [retrieved Oct. 25, 2016] (5 pages).
Casen Recordati Group, (2016), 'Cleen Ready-to-Use Enema,' emc+, medicines.org.UK/emc, XP-002763391, <https://www.medicines.org.UK/emc/history/542#version9> [retrieved Oct. 25, 2016] (2 pages).
Clark et al., (1989) "Validation of the General Purpose Tripos 5.2 Field," J. Comput Chem, 10(8):982-1012.
Collino et al., (2006) "Modulation of the Oxidative Stress and Inflammatory Response by PPAR-gamma Agonists in the Hippocampus of Rats Exposed to Cerebral Ischemia/Reperfusion," Eur J Pharmacol, 530(1-2):70-80.
Corse et al., (1948) "Biosynthesis of Penicillins" J Am Chem Soc, 70(9):2837-43.
Database CA [Online] Chemical Abstracts Service, Columbus Ohio, US; Database Accession No. 67:50608 Abstract of Baker et al.: "Irreversible Enzyme Inhibitors. LXXXVII. Hydrophobic Bonding to dihydrofolic reductase. 9. Mode of Binding of m-aryloxyalkyl groups on, 6-diamino-1,2-dihydro-2,2-dimethyl-1-phenyl-s-triazine", (1967).
Database CA [Online] Chemical Abstracts Service, Columbus, Ohio, US, Database Accession No. 107:235800, Abstract of Cleary, et al., "Methylenecyclopropane rearrangement as a probe for free radical substituent effects . . . sigma . . . bul. Values for commonly encountered conjugating and organometallic groups", (1987).
Database CA [Online] Chemical Abstracts Service, Columbus, Ohio, US, Database Accession No. 111:153586, Abstract of Gonzalez, et al., ".alpha.-Amino carbanions. A second generation formamidine for facile deprotonation leading to .alpha.-quaternary substitution", (1989).
Database CA [Online] Chemical Abstracts Service, Columbus, Ohio, US, Database Accession No. 119:95018, Abstract of Yoon, et al., "Reduction of nitro compounds with borohydride exchange resin—nickel acetate", (1993).

(56) References Cited

OTHER PUBLICATIONS

Database CA [Online] Chemical Abstracts Service, Columbus, Ohio, US, Database Accession No. 131:144358, Abstract of Lamy-Pitara, et al., "Selective Catalytic Hydrogenation of Unsaturated Derivatives of Nitrobenzene in Alcoholic Media", (1999).
Database CA [Online] Chemical Abstracts Service, Columbus, Ohio, US, Database Accession No. 50:52519, Abstract of Pratt, et al., "Reaction rates by distillation. VI. The etherification of benzyl and related alcohols", (1956).
Database CA [Online] Chemical Abstracts Service, Columbus, Ohio, US, Database Accession No. 8:526, Abstract of Schepss, "Electrolytic reduction of aldehydes", (1914).
Database CA [Online] Chemical Abstracts Service, Columbus, Ohio, US, Database Accession No. 2010:351508, Abstract of Baroni, et al., "Compounds for the selective treatment of intestinal immuninflammatory component of the celiac disease", (2007).
Database CA [Online] Chemical Abstracts Service, Columbus, Ohio, US, Database Document No. 118:101608, Accession No. 1993:101608, Abstract of Breuer, et al., "An efficient synthesis of ethyl 3'-aminocinnamate", (1992).
Database CA [Online] Chemical Abstracts Service, Columbus, Ohio, US: Database Accession No. 96:19761, Abstract of Macek et al., "Studies on Local Anesthetics LXXIV. Basic esters of o-(m-)(alkoxymethyl)carbanilic acids", (1981).
Database CA [Online] Chemical Abstracts Service, Columbus, Ohio, US; Database Accession No. 105:24135, Abstract of Wulff, et al., "Chemistry of binding sites. VI. On the suitability of various aldehydes and ketones as binding sites for monoalcohols", (1986).
Database CA [Online] Chemical Abstracts Service, Columbus, Ohio, US; Database Accession No. 110:194186, Abstract of Pei et al., "A Lewis acid catalyst supported by polymers-styrene-methyl methacrylate copolymer-titanium tetrachloride complex preparation and uses in organic synthesis", (1989).
Database CA [Online] Chemical Abstracts Service, Columbus, Ohio, US; Database Accession No. 112:157479, Abstract of Joshi et al., "Catalysis by heteropoly acids: some new aspects", (1989).
Database CA [Online] Chemical Abstracts Service, Columbus, Ohio, US; Database Accession No. 121:204747, Abstract of Yang et al., "Photosolvolysis of 2-aminobenzyl alcohol in aqueous solution", (1994).
Database CA [Online] Chemical Abstracts Service, Columbus, Ohio, US; Database Accession No. 131:228419, Abstract of Engell et al., "The Decomposition of methyl hemiacetals of benzaldehyde in aqueous solution: a study of the effect of aromatic substitution", (1999).
Database CA [Online] Chemical Abstracts Service, Columbus, Ohio, US; Database Accession No. 135:180359, Abstract of Pitts et al., "Indium metal as a reducing agent in organic synthesis", (2001).
Database CA [Online] Chemical Abstracts Service, Columbus, Ohio, US; Database Accession No. 49:68907, Abstract of Mann, et al., "The action of magnesium and of Grignard reagents on certain benzyl ethers. II. The action of Grignard reagents on .omicron.-, m-, and p-(methoxy- and phenoxymethyl) anilines", (1954).
Database CA [Online] Chemical Abstracts Service, Columbus, Ohio, US; Database Accession No. 66:37529, Abstract of Minisci, et al., "Orientation in the radical amination of aromatic compounds with N-chlorodimethylamine-competition between nuclear and benzylic attack", (1966).
Database CA [Online] Chemical Abstracts Service, Columbus, Ohio, US; Database Accession No. 84:4573, Abstract of Gale, et al., "Amidomethylation of some N,N-dialkylanilines (Tscherniac-Einhorn reaction)", (1975).
Database CA Registry [Online] Chemical Abstracts Service, Columbus, Ohio, US; Database Accession No. 1001756-73-5, Abstract & "Allichem Catalog" Jun. 3, 2009; XP002595814, (2008).
Database Caplus Chemical Abstracts Service, Columbus, Ohio, US; Database Accession No. 1913:10241, Abstract of Heller: Berichte der Deutschen Chemischen Gesellschaft (1913), 46:280-294.
Database Caplus Chemical Abstracts Service, Columbus, Ohio, US; Database Accession No. 1949:23214, Abstract of Tomcsik et al.: Helvetica Chimica Acta (1949), 32:31-34.
Database Caplus Chemical Abstracts Service, Columbus, Ohio, US; Database Accession No. 1955:19868, Abstract of Mann et al.: Chemistry & Industry (London, United Kingdom) (1954) 373-374.
Database Caplus Chemical Abstracts Service, Columbus, Ohio, US; Database Accession No. 1979:18291, Abstract of Brown et al.: "Affinity Chromatography of L-lactate dehydrogenase (LDH) on Synthetic Supports. Preparation and Immobilization of D- and L-p-aminophenyllactic Acids, New Effectors of LDH." Comptes Rendus des Seances de l'Academic des Scie. 287(4):125-128 (1978).
Database Caplus Chemical Abstracts Service, Columbus, Ohio; Database Accession No. 1925:25469, Abstract of Sherwin: "Acetylation as a Physiologic Reaction." Proceedings of the Society for Experimental Biology and Medicine (1924), 22:182.
Database Caplus Chemical Abstracts Service, Columbus, Ohio; Database Accession No. 1967:490291, Abstract of Deljac et al.: "Absolute Configuration of (--)-βhydroxy-β-(m-hydroxyphenyl) propionic acid", Recueill des Travaux Chimiques des Pays-Bas (1967), 68(8):765-768.
Database Chemcats [Online] Chemical Abstracts Service, Columbus, Ohio, US; Accession No. 2058162244, Allichem Product List, Jun. 3, 2009; XP002591674, Feb. 6, 2008.
Delbarre et al., (1964), Chemical Abstracts, vol. 65, Columbus , Ohio, Abstract No. 93711, "Non-steroid Antiinflammatory Substances. I. Derivatives of the 4- and 5- Aminosalicylic Acids," Med Exp Int J Exp Med, 11:389-96.
Delijac et al., (1967) "Absolute Configuration of (−)-β-Hydroxy-β-(m)-Hydroxyphenyl)-Propionic Acid," Recueil des Travaux Chimiques des Pays-Bas, 86:765-8.
Dimon-Gadal et al., (2000) 'Increased Oxidative Damage to Fibroblasts in Skin With and Without Lesions in Psoriasis,' J Invest Dermatol,114(5):984-9.
DiPoï et al., (2004) 'Functions of Peroxisome Proliferator-Activated Receptors (PPAR) in Skin Homeostasis,' Lipids, 39(11):1093-9.
DiPoï et al., (2005) 'Epithelium-Mesenchyme Interactions Control the Activity of Peroxisome Proliferator-Activated Receptor β/δ During Hair Follicle Development,' Mol Cell Biol, 25(5):1696-1712.
Doshi et al., (1997) "A Comparison of Current Acne Grading Systems and Proposal of a Novel System,"Int J Dermatol, 36(6):416-8.
Drosner M et al., (2005), 'Photo-Epilation: Guidelines for Care from the European Society for Laser Dermatology (ESLD),' J Cosmet Laser Ther, 7(1):33-8.
Dubuquoy et al., (2002) "Role of peroxisome proliferator-activated receptor γ and retinoid X receptor heterodimer in hepatogastroenterological diseases," Lancet, 360(9343):1410-8.
Dubuquoy et al., (2003) "Impaired Expression of Peroxisome Proliferator-Activated Receptor Gamma in Ulcerative Colitis," Gastroenterology, 124(5):1265-76.
Egan et al., (2003) "Clinical Pharmacology in Inflammatory Bowel Disease: Optimizing Current Medical Therapy," *Inflammatory Bowel Disease: From Bench to Bedside*, ($2^{nd}$Ed, 2003), Stephan R Targan et al. (Eds), Springer Publishingm New York, NY (Publ), pp. 495-521.
Ellis et al., (2007) "Placebo Response in Two Long-Term Randomized Psoriasis Studies that were Negative for Rosiglitazone," Am J Clin Dematol, 8(2):93-102.
European Clinical Trials Register, (2012), entry EudraCT No. 2011-003283-78 [online] Mar. 1 2012, [retrieved from the internet at <https://www.clinicaltrialsregister.eu/ctr-search/trial/2011-003283-78/IT>on Feb. 1, 2017] European Union Clinical Trials Register, XO-002766683 (6 pages).
Examination Report dated Apr. 15, 2011 for Application No. 06 766 083.7-2103 (11 pages).
Fernholz et al., (1992) "Specificity of Antibody-Catalyzed Transesterifications Using Enol Esters: A Comparison with Lipase Reactions," J Org Chem, 57(17):4756-61.
Floch and White, (2006), 'Management of Diverticular Disease is Changing,' World J Gastroenterol, 12(20):3225-8.

(56) References Cited

OTHER PUBLICATIONS

Fuenzalida et al., (2007) "Peroxisome Proliferator-activated Receptor Gamma Up-regulates the Bcl-2 Anti-apoptotic Protein in Neurons and Induces Mitochondrial Stabilization and Proection against Oxidative Stress and Apoptosis," J Biol Chem, 282(51):37006-15.
Gampe et al., (2000) "Asymmetry in the PPARγ/RXRα Crystal Structure Reveals the Molecular Basis of Heterodimerization Among Nuclear Receptors," Mol Cell, 5(3):545-55.
Garza LA et al., (2011), 'Bald Scalp in Men with Androgenetic Alopecia Retains Hair Follicle Stern Cells but Lacks CD200-Rich and CD34-Positive Hair Follicle Progenitor Cells,' J Clin Invest, 121(2):613-22.
Gerdes et al., (1986) "Growth Fractions in Breast Cancers Determined in Situ with Monoclonal Antibody Ki-67," J Clin Pathol, 39(9):977-80.
Gormin (1989), "Picosecond Transient Absorption Spectra of Aminosalicylates in Confirmation of the Triple Excitation Mechanism," J Phys Chem, 93(16):5979-80.
Guo et al., (2009) "Effect of Uyghur Compound Xipayi Kui Jie' an on the Ultrastructure of Small Intestinal Epithelial Cell in Rat Model of Ulcerative Colitis," J Xinjiang Medi Univ, 32(7):893-4.
Harari (2004) "Epidermal Growth Factor Receptor Inhibition Strategies in Oncology," Endocr Relat Cancer, 11(4):689-708.
Harrington et al., (2008) 'A Re-appraisal of Lactose Intolerance,' Int J Clin Pract, 62(10):1541-6.
Husova et al., (2007) "Hepatopathy, Coeliac Disease and Lymphocytic Colitis," Ceska A. Slovenska Gastroenterologie A. Hepatologie—CZ SL Gastroenterol Hepatol, 61(6):309-13.
International Preliminary Report on Patentability and Written Opinion of the International Searching Authority for PCT/IE2006/000076, dated Jan. 22, 2008 (10 pages).
International Preliminary Report on Patentability and Written Opinion of the International Searching Authority for PCT/EP13/057729, dated Oct. 21, 2014 (6 pages).
International Preliminary Report on Patentability and Written Opinion of the International Searching Authority for PCT/EP2009/008631, dated Jun. 7, 2011(13 pages).
International Preliminary Report on Patentability and Written Opinion of the International Searching Authority for PCT/EP2009/008633, dated Jun. 7, 2011 (6 pages).
International Preliminary Report on Patentability and Written Opinion of the International Searching Authority for PCT/EP2010/000935, dated Aug. 16, 2011 (7 pages).
International Preliminary Report on Patentability and Written Opinion of the International Searching Authority for PCT/EP2010/000939, dated Aug. 16, 2011 (8 pages).
International Preliminary Report on Patentability and Written Opinion of the International Searching Authority for PCT/EP2013/052617, dated Aug. 12, 2014 (5 pages).
International Preliminary Report on Patentability and Written Opinion of the International Searching Authority for PCT/EP2013/069062, dated Mar. 17, 2015 (7 pages).
International Preliminary Report on Patentability and Written Opinion of the International Searching Authority for PCT/EP2013/069063, dated Mar. 17, 2015 (7 pages).
International Preliminary Report on Patentability and Written Opinion of the International Searching Authority for PCT/IE2006/000078, dated Jan. 22, 2008 (14 pages).
International Preliminary Report on Patentability and Written Opinion of the International Searching Authority for PCT/EP2008/052354, dated May 22, 2009 (20 pages).
International Preliminary Report on Patentability and Written Opinion of the International Searching Authority for PCT/EP2008/068265, dated Apr. 12, 2010 (11 pages).
International Search Report and Written Opinion of the International Searching Authority for International Application No. PCT/EP2016/079512, dated Feb. 28, 2017 (15 pages).
International Search Report and Written Opinion of the International Searching Authority for International Application No. PCT/IE2006/000078, dated Jan. 26, 2007 (14 pages).
International Search Report for PCT/EP2008/052354, dated Jun. 9, 2008 (6 pages).
International Search Report for PCT/EP2008/068265, dated Aug. 11, 2009 (5 pages).
International Search Report for PCT/EP2009/008631, dated Aug. 19, 2010 (9 pages).
International Search Report for PCT/EP2009/008633, dated Feb. 22, 2010 (4 pages).
International Search Report for PCT/EP2010/000935, dated Aug. 23, 2010 (5 pages).
International Search Report for PCT/EP2010/000939, dated Sep. 20, 2010 (5 pages).
International Search Report for PCT/EP2013/052617, dated Aug. 12, 2014 (4 pages).
International Search Report for PCT/EP2013/057729, dated Jun. 11, 2013 (4 pages).
International Search Report for PCT/EP2013/069062, dated Dec. 10, 2013 (3 pages).
International Search Report for PCT/EP2013/069063, dated Dec. 20, 2013 (3 pages).
International Search Report for PCT/IE2006/000076, dated Feb. 1, 2007 (5 pages).
Ireland et al., (1992) "Comparison of 5-Aminosalicylic Acid and N-Acetylaminosalicylic Acid Uptake by the Isolated Human Colonic Epithelial Cell," Gut, 33(10):1343-7.
Janda et al., (1988) "Antibody Catalysis of Bimolecular Amide Formation," J Am Chem Soc, 110(14):4835-7.
Johnson et al., (2012) 'Intestinal Fibrosis is Reduced by Early Elimination of Inflammation in a Mouse Model of IBD: Impact of a "Top-Down" Approach to Intestinal Fibrosis in Mice,' Inflamm Bowel Dis, 18(3):460-71.
Jones et al., (1997) "Development and Validation of a Genetic Algorithm for Flexible Docking," J Mol Biol, 267(3):727-48.
Julien et al., (2005) 'Antifibrogenic Role of the Cannabinoid Receptor CB2 in the Liver,' Gastroenterology, 128(3):742-55.
Kari et al., (2003) "Targeting the Epidermal Growth Factor Receptor in Cancer: Apoptosis Takes Center Stage," Cancer Res, 63(1):1-5.
Karnik et al., (2009) 'Hair Follicle Stem Cell-specific PPARγ Deletion Causes Scarring Alopecia,' J Invest Dermatol, 129(5):1243-57.
Kloepper et al., (2008) 'Immunophenotyping of the Human Bulge Region: The Quest to Define Useful in situ Markers for Human Epithelial Hair Follicle Stem Cells and their Niche,' Exp Dermatol, 17(7):592-609.
Koeffler, (2003), "Peroxisome Proliferator-activated Receptor γ and Cancers," Clin Cancer Res, 9(1):1-9.
Kuenzli and Seurat, (2003) 'Effect of Topical PPARγ/δ and PPARγ Agonists on Plaque Psoriasis: A Pilot Study,' Dermatology, 206(3):252-6.
Lavker RM et al., (2003), 'Hair Follicle Stem Cells,' J Investig Dermatol Symp Proc, 8(1):28-38.
Lees et al., (2008) 'Analysis of Germline GLI1 Variation Implicates Hedgehog Signalling in the Regulation of Intestinal Inflammatory Pathways,' PLoS Med, 5(12):e239 (15 pages).
Li L and Xie T, (2005), 'Stem Cell Niche: Structure and Function,' Annu Rev Cell Dev Biol, 21:605-31.
Liao et al.,(1990) 'Therapeutic Effect of Methyl 5-Aminosalicylate on Experimental Ulcerative Colitis in Rabbits,' Acta Pharmacologica Sinica 11(1):54-6.
Lin et al., (1998) "An Antibody Transesterase Derived from Reactive Immunization that Utilizes a Wide Variety of Alcohol Substrates," Chem Commun, 10:1075-6.
Lowe, D. (2009) "More Binding Site Weirdness," CORANTE: In the Pipeline, pp. 1-4.
Mager et al., (1979) "Struktur-Wirkungs-Beziehungen bei Salizylsaure- und Benzoesaurederivaten," Zbl. Pharm. 118(Heft 12):1259-75 (concise explanation of relevance attached).
Mandt N et al.,(2005), 'Epilation Today: Physiology of the Hair Follicle and Clinical Photo-Epilation,' J Investig Dermatol Symp Proc, 10(3):271-4.
Mangelsdorf et al., (1995) "The Nuclear Receptor Superfamily: The Second Decade," Cell, 83(6): 835-9.

(56) References Cited

OTHER PUBLICATIONS

Medline Database, (2013), U.S. National Library of Medicine, Bethesda, MD, XP002763389, Accession No. NLM23651165, Benjamin B et al., 'PPAR-gamma in Ulcerative Colitis: A Novel Target for Intervention,' Curr Drug Targ, 14(12):1501-7.
Medow et al., (1990) 'γ-Galactosidase Tablets in the Treatment of Lactose Intolerance in Pediatrics,' Am J Dis Child, 144(11):1261-4 (ABSTRACT).
Meek et al., (1969) "Carboxylation of Substituted Phenols in N,N-Dimethylamide Solvents at Atmospheric Pressure," J Chem Eng Data, 14(3):388-91.
Mendelsohn (2001) "The Epidermal Growth Factor Receptor as a Target for Cancer Therapy," Endocr Relat Cancer, 8(1):3-9.
Merck Manual Home Edition, "Ulcerative Colitis", Merck Sharp & Dohme Corp., Copyright © 2004-2011 pp. 1-6 [online] [retrieved on Apr. 19, 2013] Retrieved from http://www.merckmanuals.com/home/print/digestive_disorders/inflammatory_bowel_diseases_ibd/ulcerative_colitis.html.
Michalik and Wahli, (2007) 'Peroxisome Proliferator-activated Receptors (PPARs) in Skin Health, Repair and Disease,' Biochim Biophys Acta, 1771(8):991-8.
Misra et al., (2002) "Phosphorylation of Transcriptional Coactivator Peroxisome Proliferator-Activated Receptor (PPAR)-Binding Protein (PBP). Stimulation of Transcriptional Regulation by Mitogen-Activated Protein Kinase," J Biol Chem, 277(50): 48745-54.
Nolte et al., (1998) "Ligand Binding and Co-Activator Assembly of the Peroxisome Proliferator-Activated Receptor-γ," Nature, 395(6698):137-43.
O'Mahony, et al., (1990) "Coeliac Disease and Collagenous Colitis," Postgrad Med, 66(773):238-41.
Office Action issued in Japanese Patent Application No. 2011-549494 dated Feb. 25, 2014, with English language translation (8 pages).
Osawa et al., (2003) "Peroxisome Proliferator-Activated Receptor γ Ligands Suppress Colon Carcinogenesis Induced by Azoxymethane in Mice," Gastroenterology, 124(2):361-7.
Oshima H et al., (2001), 'Morphogenesis and Renewal of Hair Follicles from Adult Multipotent Stem Cells,' Cell, 104(2):233-45.
Pedersen et al., (2010) 'Topical Rosiglitazone Treatment Improves Ulcerative Colitis by Restoring Peroxisome Proliferator-Activated Receptor-γ Activity,' Am J Gastroenterol, 105(7):1596-1603 (Abstract).
Pershadsingh et al., (2005) 'Improvement in Psoriasis with Rosiglitazone in a Diabetic and a Nondiabetic Patient,' Skinmed, 4(6):386-90 (Abstract).
Peyrin-Biroulet et al., (2010), 'Peroxisome Proliferator-Activated Receptor Gamma Activation is Required for Maintenance of Innate Antimicrobial Immunity in the Colon,' Proc Natl Acad Sci USA, 107(19):8772-7.
Peyrin-Biroulet, et al. (2007) "Peroxisome Proliferator-Activated Receptor Gamma Functions as an Antibacterial Factor," J Crohns Colitis Suppl, 1(1):2.
Ponchant et al., (1991) Synthesis of 5-[$^{125}$I]-Iodo-Zacopride, a New Probe for 5-HT$_3$ Receptor Binding Sites, Journal of Labelled Compounds and Radiopharmaceuticals, 29(10):1147-55.
Porter and Ihrig, (1923), 'Asymmetric Dyes,' J Am Chem Soc, 45(8):1990-3 (Abstract only).
Ramprasad et al., (2002) 'Sustained-Delivery of Apolipoprotein E-peptidomimetic Using Multivesicular Liposomes Lowers Serum Cholesterol Levels,' J Control Release, 79(1-3):207-18.
Reifen, Ram, et al. (2004) "5-ASA and Lycopene Decrease the Oxidative Stress and Inflammation Induced by Iron in Rats with Colitis," J Gastroenterol, 3996):514-9.
Result Summary for Study ID No. SB-999910/150 (2002) "A Study in Patients with Crohn's Disease to Evaluate the Effect of AVANDIA™ on Inflammatory Activity Mediated by Monocytes/Macrophages" Retrieved from: download.gsk-clinicalstudyregister.com/files/23093.pdf on May 23, 2012 (2 pages).
Risérus et al., (2008) "Activation of Peroxisome Proliferator-activated Receptor (PPAR) Delta Promotes Reversal of Multiple Metabolic Abnormalities, Reduces Oxidative Stress, and Increases Fatty Acid Oxidation in Moderately Obese Men," Diabetes, 57(NR. 2):332-9.
Ritland et al., (1999) 'Evaluation of 5-Aminosalicylic Acid (5-ASA) for Cancer Chemoprevention: Lack of Efficacy against Nascent Adenomatous Polyps in the Apc$^{Min}$ Mouse,' Clin Cancer Res, 5(4):855-63.
Robertson et al., (1985) 'Structure-Activity Relationships of Arylimidazopyridine Cardiotonics: Discovery and Inotropic Activity of 2-[2-Methoxy-4-(methylsulfinyl)phenyl]-1H-imidazo[4,5-c]pyridine,' J Med Chem, 28(6):717-27.
Rousseaux et al., (2005) "Intestinal Anti-inflammatory Effect of 5-Aminosalicylic Acid is Dependent on Peroxisome Proliferator-Activated Receptor-γ," J Exp Med, 201(8):1205-15.
Rousseaux et al., (2010), 'Preclinical and Toxicological Assessments of the Novel Orally Bioavailable PPAR Ligand GED-0507-34-Levo for the Treatment of Inflammatory Bowel Disease,' Gastroenterology 2010 DDW Abstract Supplement, AGA Abstract #1080, 138(5—Suppl 1):S-157.
Rousseaux et al., (2011) 'Preclinical Evaluation of Intestinal Anti-Inflammatory/Analgesic Properties and Phase I Clinical Trial of a New PPAR Agonist Ged-0507-34-Levo,' Gastroenterology, 140(5):S-515 (Abstract).
Rovner (2009) "An Enzyme Reveals an Unexpected Inclusiveness, Protein Binding: Bacterial Enzyme's Active Site Welcomes Both Enantiomers of a Chiral Molecule at the Same Time," Chem Eng News, Nov 5, 2009 issue, (2 pages) retieved from http://cen.acs.org/articles/87/web/2009/11/Enzyme-Reveals-Unexpected-Inclusiveness.html?type=paidArticleContent.
Schauber J et al., (2004) 'Histone-Deacetylase Inhibitors Induce the Cathelicidin LL-37 in Gastrointestinal Cells,' Mol Immunol, 41(9):847-54.
Schwab et al., (2007) 'Role of Nuclear Hormone Receptors in Butyrate-Mediated Up-Regulation of the Antimicrobial Peptide Cathelicidin in Epithelial Colorectal Cells,' Mol Immunol, 44(8):2107-14.
Sherwin (1924), "Acetylation as a Physiologic Reaction," Proc Soc Exper Biol & Med, 22:182.
Speca et al., (2012) 'Cellular and Molecular Mechanisms of Intestinal Fibrosis,' World J Gastroenterol, 18(28):3635-61.
Tanaka et al.,(2001) "Ligands for Peroxisome Proliferator-Activated Receptors α and γ Inhibit Chemically Induced Colitis and Formation of Aberrant Crypt Foci in Rats," Cancer Res., 61(6): 2424-8.
Tosti et al., (2009) 'Treatment Strategies for Alopecia,' Expert Opin Pharmacother, 10(6):1017-26.
Troilius A and Troilius C, (1999), 'Hair Removal with a Second Generation Broad Spectrum Intense Pulsed Light Source—A Long Term Follow-up,' J Cutan Laser Ther, 1(3):173-8.
Tuleu, et al., (2002) "Colonic Delivery of 4-Aminosalicylic Acid Using Amylose-Ethyl Cellulose-Coated Hydroxypropyl Methyl Cellulose Capsules," Aliment Pharmacol Ther., 167(10):1771-9.
Tursi et al., (2002), 'Long-Term Treatment with Mesalazine and Rifaximin Versus Rifaximin Alone for Patients with Recurrent Attacks of Acute Diverticulitis of Colon,' Digest Liver Dis, 34(7):510-5.
Tursi, (2004), 'Acute Diverticulitis of the Colon—Current Medical Therapeutic Management,' Exp Opin Pharmacother, 5(1):55-9.
Tzameli et al., (2004) 'Regulated Production of a Peroxisome Proliferator-Activated Receptor-γ Ligand During an Early Phase of Adipocyte Differentiation in 3T3-L1 Adipocytes,' J Biol Chem, 279(34):36093-102.
van't Riet, Bart, et al. (1979) "Synthesis of Hydroxy and Amino-Substituted Benzohydroxamic Acids: Inhibition of Ribonucleotide Reductase and Antitumor Activity," J Med Chem, 22(5) 589-92.
Venkatraman et al., (2004) 'Alpha-Lipoic Acid-Based PPARγ Agonists for Treating Inflammatory Skin Diseases,' Arch Dermatol Res, 296(3):97-104 (Abstract).
Wallace et al., (1989) 'Inhibition of Leukotriene Synthesis Markedly Accelerates Healing in Rat Model of Inflammatory Bowel Disease,' Gastroenterology, 96(1):29-36.

(56) References Cited

OTHER PUBLICATIONS

Wang et al., (2002) "Further Development and Validation of Emphirical Scoring Functions for Structure-Based Binding Affinity Prediction," J Comput Aided Mol Des, 16(1):11-26.
Wang et al.,(2004) 'Cutting Edge: 1,25-Dihydroxyvitamin D3 is a Direct Inducer of Antimicrobial Peptide Gene Expression,' J Immunol, 173(5):2909-12.
Wei et al., (2010) 'Peroxisome Proliferator-Activated Receptor γ: Innate Protection from Excessive Fibrogenesis and Potential therapeutic Target in Systemic Sclerosis,' Curr Opin Rheumatol, 22(6):671-6 (HHS Public Access version of Author Manuscript).
Westin et al., (1998) "Interactions Controlling the Assembly of Nuclear-Receptor Heterodimers and Co-Activators," Nature, 395(6698):199-202.
Williams and Hallett (1989) "Effect of Sulphasalazine and its Active Metabolite, 5-Amino-Salicylic Acid, on Toxic Oxyden Metabolite Production by Neutrophils," Gut, 30(11):1581-7.
Written Opinion of the International Searching Authority for International Application No. PCT/EP2006/000076, dated Feb. 1, 2007 (9 pages).
Written Opinion of the International Searching Authority for International Application No. PCT/EP2013/052617, dated Aug. 12, 2014 (4 pages).
Written Opinion of the International Searching Authority for International Application No. PCT/EP2013/069062, dated Dec. 10, 2013 (6 pages).
Written Opinion of the International Searching Authority for International Application No. PCT/EP2013/069063, dated Dec. 29, 2013 (7 pages).
Written Opinion of the International Searching Authority for International Application No. PCT/EP2008/052354, dated Jun. 9, 2008 (10 pages).
Written Opinion of the International Searching Authority for International Application No. PCT/EP2008/068265, dated Aug. 11, 2009 (12 pages).
Wu et al., (2006) 'Effects of Rosiglitazone on Expression of TGF-A1 in Experimental Hepatic Fibrosis Rats,' Chin J Gastroenterol Hepatol, 15(2):126-9.
Xu et al.,(2001) "Structural Determinants of Ligand Binding Selectivity Between the Peroxisome Proliferator-Activated Receptors," Proc Natl Acad Sci USA, 98(24):13919-24.
Yanai et al., (2004) "Para-Position Derivatives of Fungal Anthelmintic Cyclodepsipeptides Engineered with Streptomyces Venezuelae Antibiotic Biosynthetic Genes," Nat Biotechnol, 22(7):848-55.
Youssef and Badr, (2004) "Role of Peroxisome Proliferator-Activated Receptors in Inflammation Control," J Biomed Biotechnol, 2004(3):156-66.
Yu et al., (2010) 'Peroxisome Proliferator-Activated Receptors Gamma Reverses Hepatic Nutritional Fibrosis in Mice and Suppresses Activation of Hepatic Stellate Cells in vitro,' Int J Biochem Cell Biol, 42(6):948-57.
Zhou et al., (1999) 'Intestinal Metabolism and Transport of 5-Aminosalicylate,' Drug Metab Dispos, 27(4):479-85.
U.S. Appl. No. 13/131,978, Methods for Preventing or Reducing Colon Carcinogenesis, filed Aug. 11, 2011, Abandoned.
U.S. Appl. No. 15/088,654, Methods for Preventing or Reducing Colon Carcinogenesis, filed Apr. 1, 2016, Published U.S. 2017/0056349.
U.S. Appl. No. 13/201,786, Alkylamido Compounds and Uses Thereof, filed Nov. 17, 2011, Patented U.S. Pat. No. 8,754,127.
U.S. Appl. No. 14/255,255, Alkylamido Compounds and Uses Thereof, filed Apr. 17, 2014, Patented U.S. Pat. No. 9,511,041.
U.S. Appl. No. 15/337,707, Alkylamido Compounds and Uses Thereof, filed Oct. 28, 2016, Published U.S. 2017-0172956.
U.S. Appl. No. 13/131,982, Methods of Preventing or Reducing Colon Carcinogenesis, filed Aug. 11, 2011, Patented U.S. Pat. No. 8,501,806.
U.S. Appl. No. 12/528,522, PPAR-Gamma Agonists For the Induction of Cationic Antimicrobial Peptide Expression as Immunoprotective Stimulants, filed Mar. 4, 2011, Published U.S. 2011-0152225.
U.S. Appl. No. 13/201,790, Methods of Treating Hair Related Conditions, filed Nov. 17, 2011, Patented U.S. Pat. No. 8,796,334.
U.S. Appl. No. 14/314,738, Methods of Treating Hair Related Conditions, filed Jun. 25, 2014, Abandoned.
U.S. Appl. No. 14/969,939, Methods of Treating Hair Related Conditions, filed Dec. 15, 2015, Published U.S. 2016-0338927.
U.S. Appl. No. 11/989,090, Compounds and Their Salts Specific to the PPAR Receptors and the EGF Receptors and Their Use in the Medical Field, Jun. 6, 2008, Patented U.S. Pat. No. 8,153,841.
U.S. Appl. No. 13/408,439, Compounds and Their Salts Specific to the PPAR Receptors and the EGF Receptors and Their Use in the Medical Field, filed Feb. 29, 2012, Patented U.S. Pat. No. 8,710,100.
U.S. Appl. No. 14/202,386, Compounds and Their Salts Specific to the PPAR Receptors and the EGF Receptors and Their Use in the Medical Field, filed Mar. 10, 2014, Patented U.S. Pat. No. 9,133,099.
U.S. Appl. No. 14/671,579, Compounds and Their Salts Specific to the PPAR Receptors and the EGF Receptors and Their Use in the Medical Field, filed Mar. 27, 2015, Patented U.S. Pat. No. 9,561,202.
U.S. Appl. No. 14/671,585, Compounds and Their Salts Specific to the PPAR Receptors and the EGF Receptors and Their Use in the Medical Field, filed Mar. 27, 2015, Patented U.S. Pat. No. 9,345,680.
U.S. Appl. No. 11/989,033, Compounds and Their Salts Specific to the PPAR Receptors and EGF and Their Use in the Medical Field, filed Jun. 6, 2008, Patented U.S. Pat. No. 8,138,357.
U.S. Appl. No. 13/397,245, Compounds and Their Salts Specific to the PPAR Receptors and EGF Receptors and Their Use in the Medical Field, filed Feb. 15, 2012, Patented U.S. Pat. No. 8,450,506.
U.S. Appl. No. 13/785,485, Compounds and Their Salts Specific to the PPAR Receptors and EGF Receptors and Their Use in the Medical Field, filed Mar. 5, 2013, Abandoned.
U.S. Appl. No. 12/810,159, Compounds for the Selective Treatment of the Intestinal Immuno-Inflammatory Component of the Celiac Disease, filed Aug. 16, 2010, Patented U.S. Pat. No. 8,153,693.
U.S. Appl. No. 13/331,173, Compounds for the Selective Treatment of the Intestinal Immuno-Inflammatory Component of the Celiac Disease, filed Dec. 20, 2011, Abandoned.
U.S. Appl. No. 14/377,362, Methods of Treating Fibrosis, filed Aug. 7, 2014, Patented U.S. Pat. No. 9,682,923.
U.S. Appl. No. 15/593,864, Methods of Treating Fibrosis, filed May 12, 2017, Pending.
U.S. Appl. No. 14/394,916, Methods of Treating Lactose Intolerance, filed Oct. 16, 2014, Patented U.S. Pat. No. 9,682,050.
U.S. Appl. No. 15/594,023, Methods of Treating Lactose Intolerance, filed May 12, 2017, Pending.
U.S. Appl. No. 14/428,048, Methods of Inhibiting Hair Growth, filed Mar. 13, 2015, Abandoned.
U.S. Appl. No. 14/428,164, Methods of Treating Hair Related Conditions, filed Mar. 13, 2015, Published U.S. 2015/0250749.

Structure of compounds 20, 23, 32, 33, 34, 35, 39, 40

20

23

32

33

34

35

39

40

FIG. 5: Docking of (R) Compound 34 to PPARγ receptor (amino acid residues labeling and hydrogen bonding is shown)
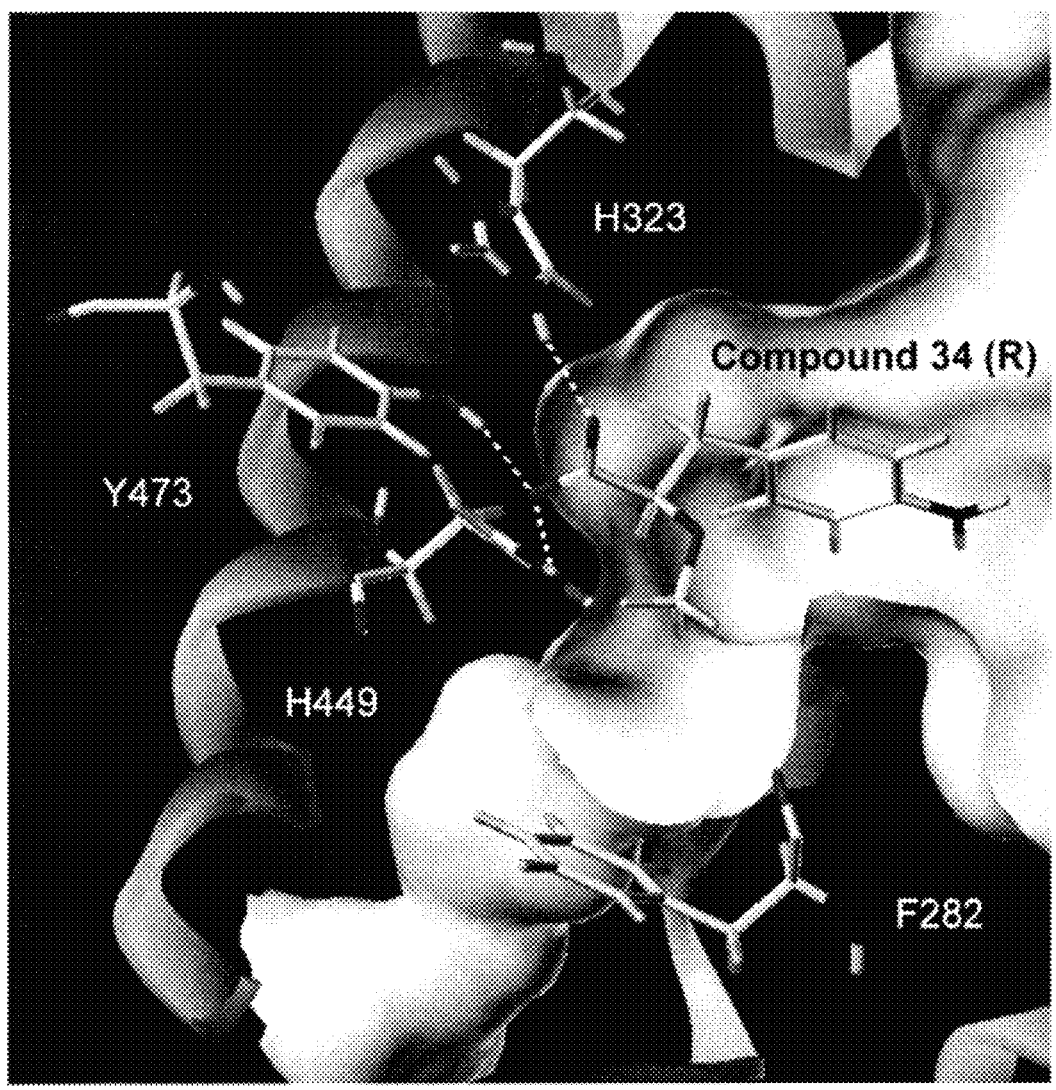

FIG. 6: Docking of (S) Compound 34 to PPARγ receptor
(amino acid residues labeling and hydrogen bonding is shown)
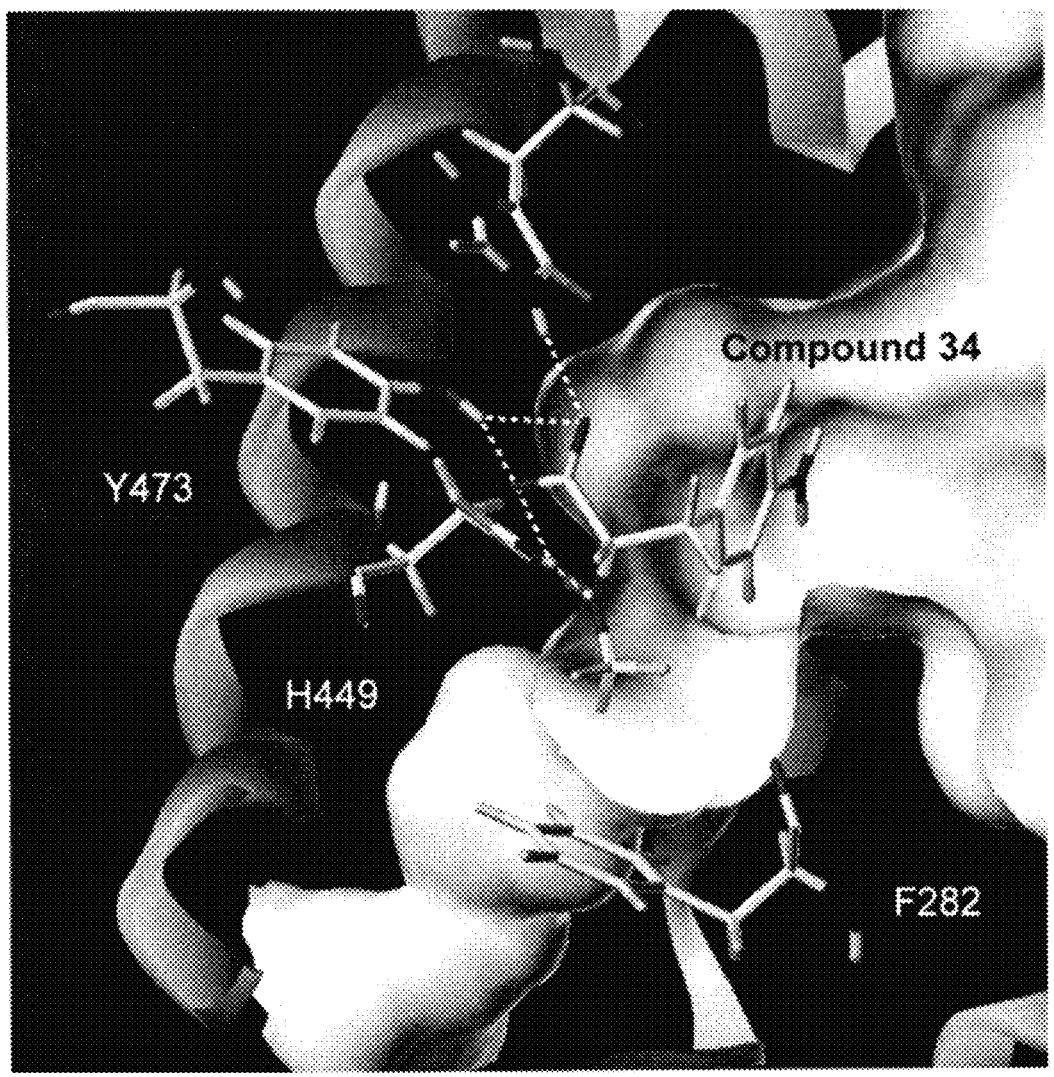

FIG. 7: Docking of (R) Compound 35 to PPARγ receptor
(amino acid residues labeling and hydrogen bonding is shown)
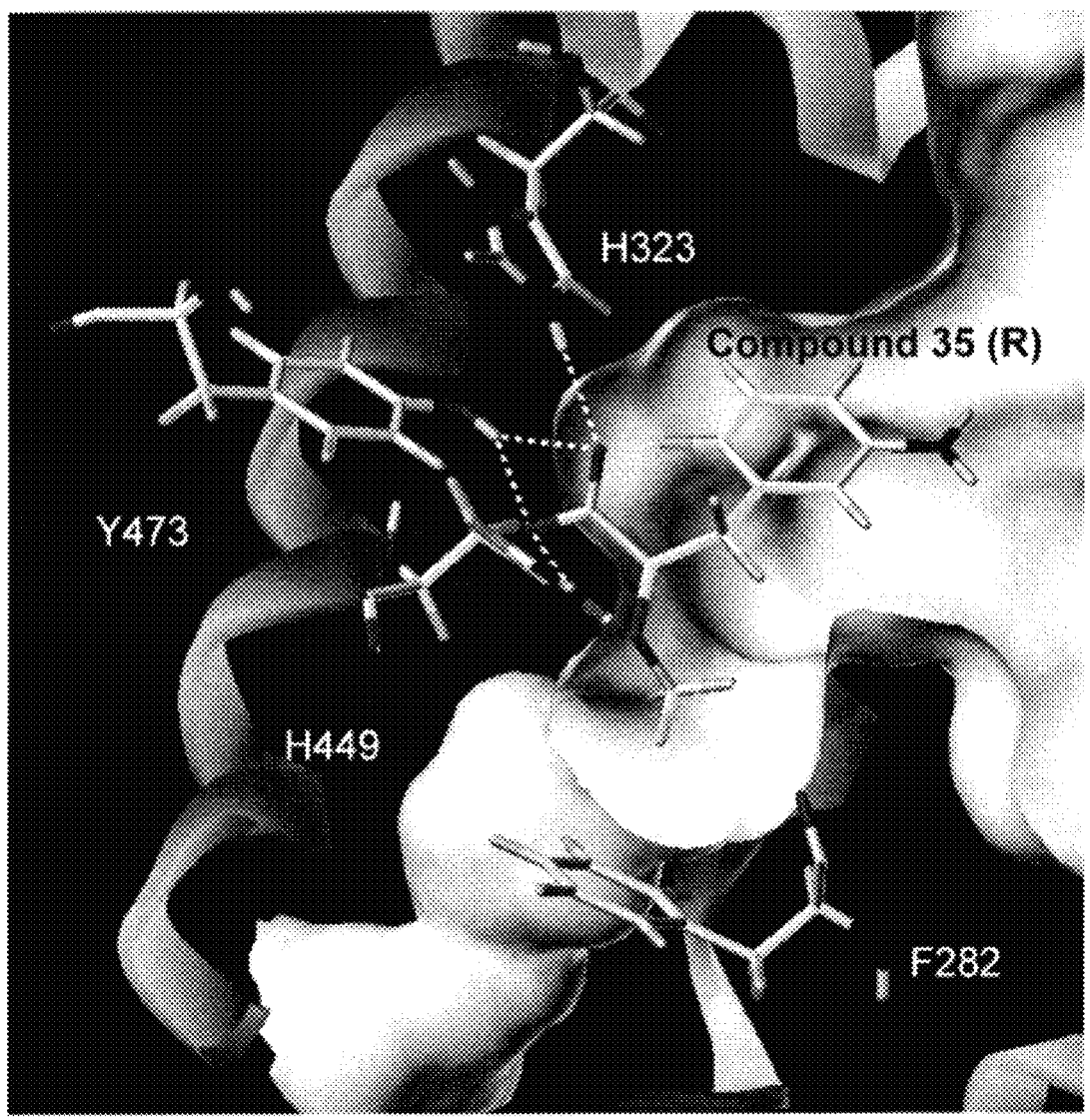

FIG. 8: Docking of (S) Compound 35 to PPARγ receptor
(amino acid residues labeling and hydrogen bonding is shown)
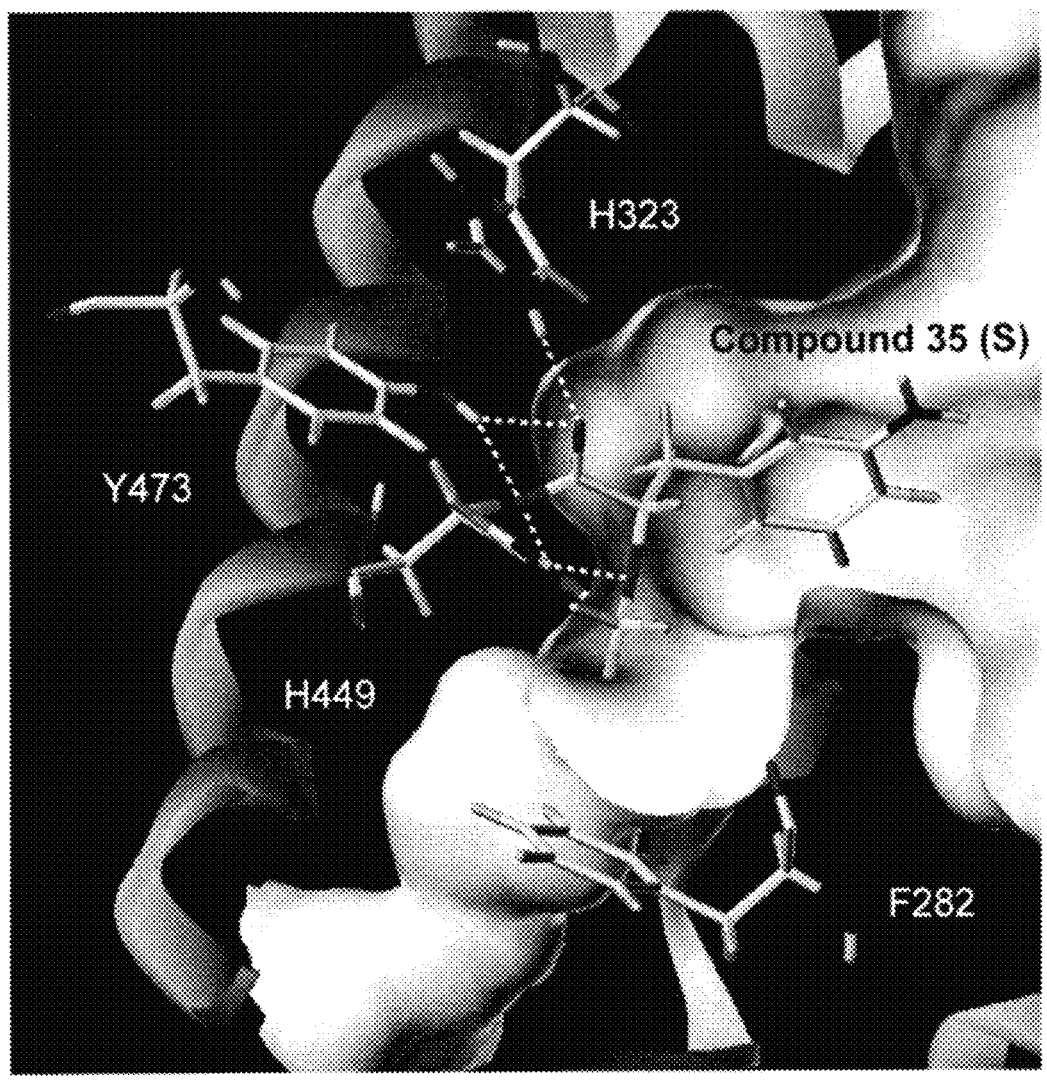

FIG. 9: Docking of (R) Compound 39 to PPARγ receptor (amino acid residues labeling and hydrogen bonding is shown)
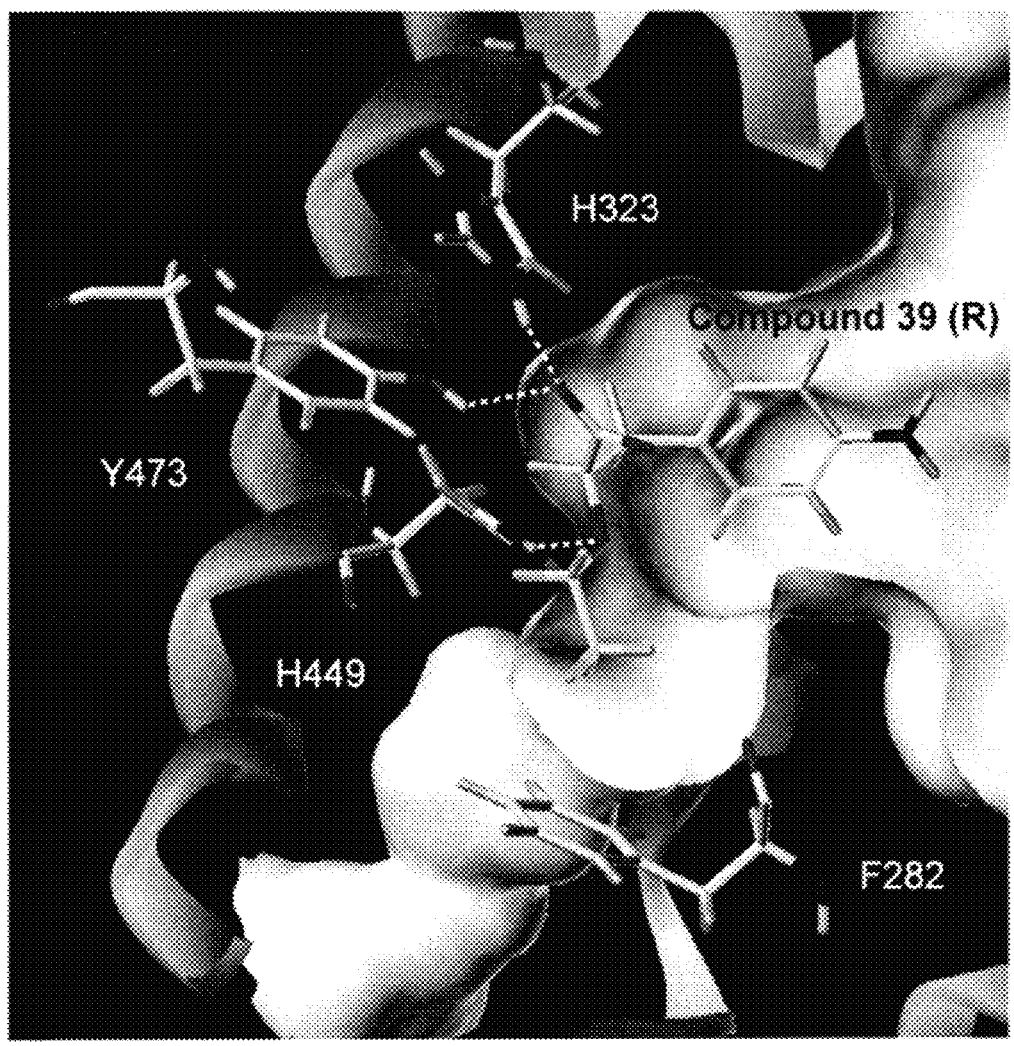

FIG. 10: Docking of (S) Compound 39 to PPARγ receptor
(amino acid residues labeling and hydrogen bonding is shown)
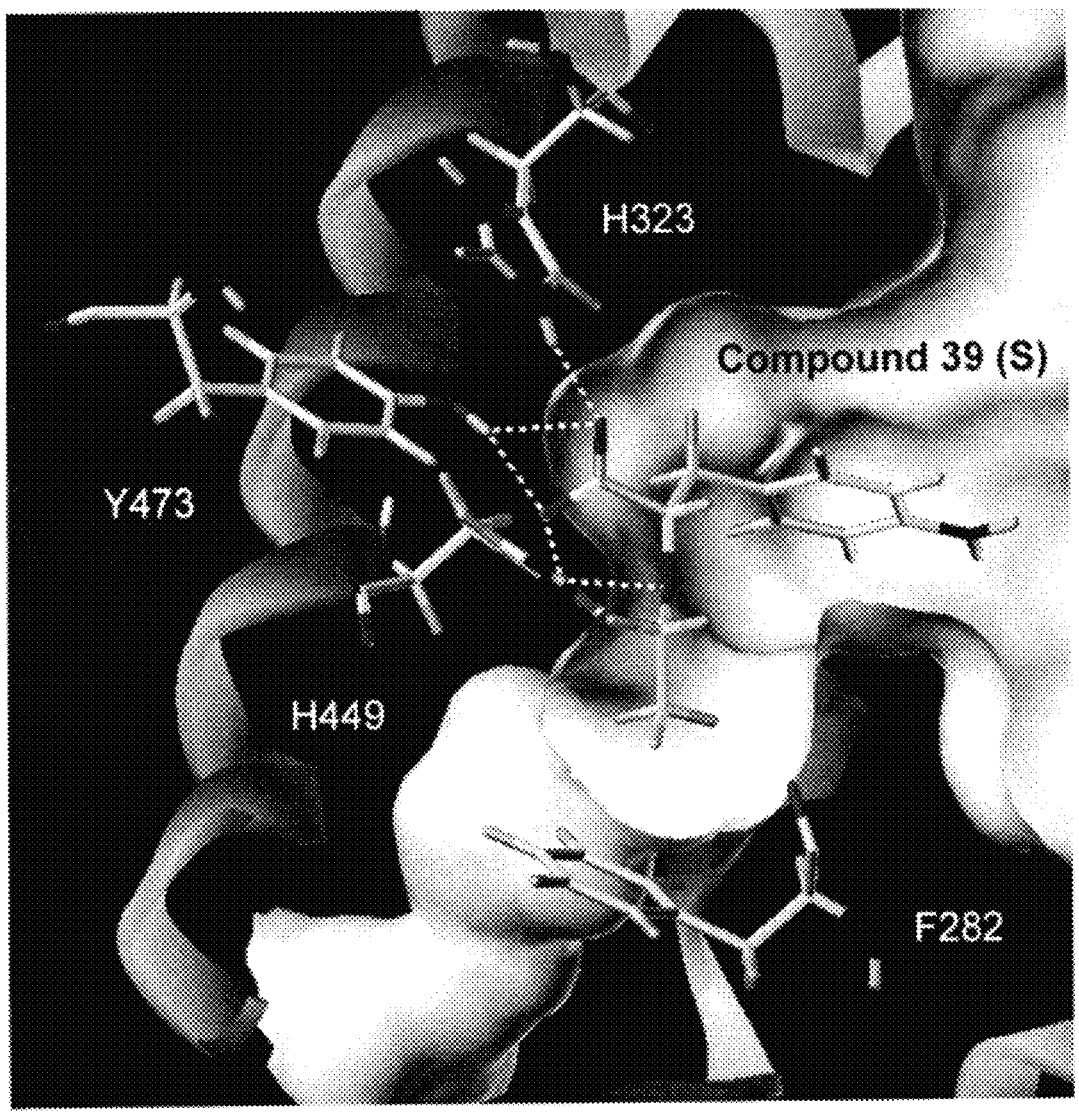

FIG. 11: Docking of 5-aminosalicylic acid (mesalamine) to PPARγ receptor (amino acid residues labeling is shown)
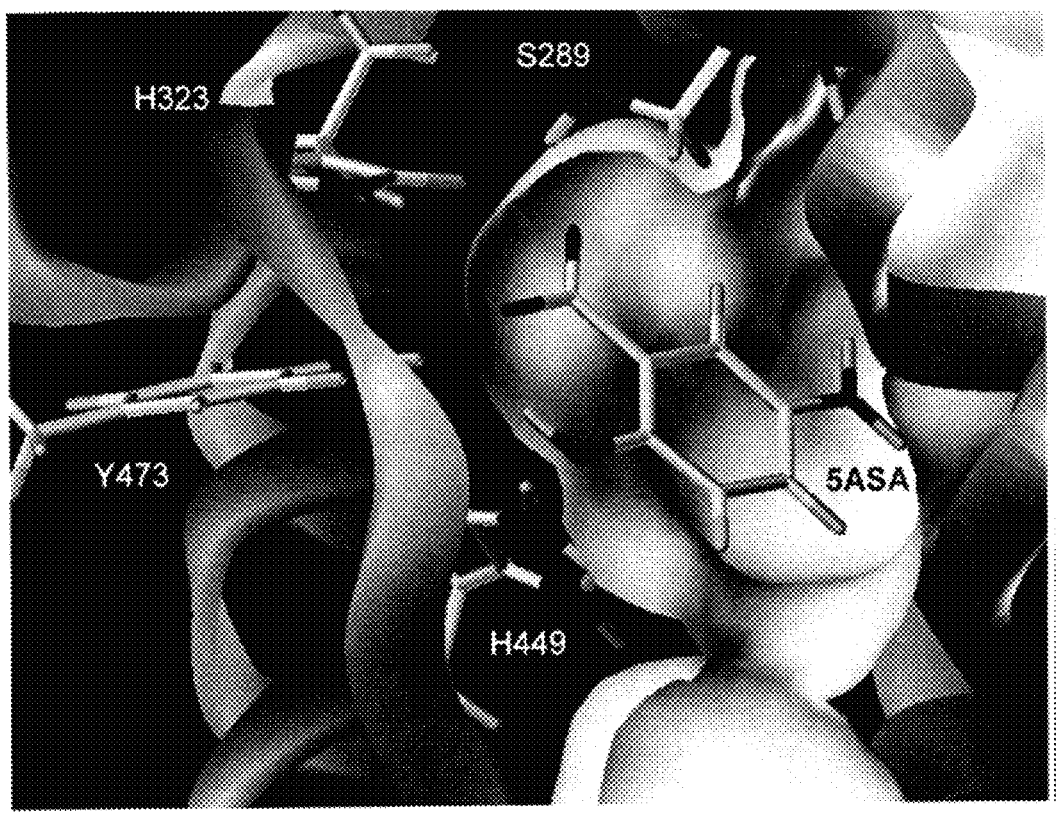

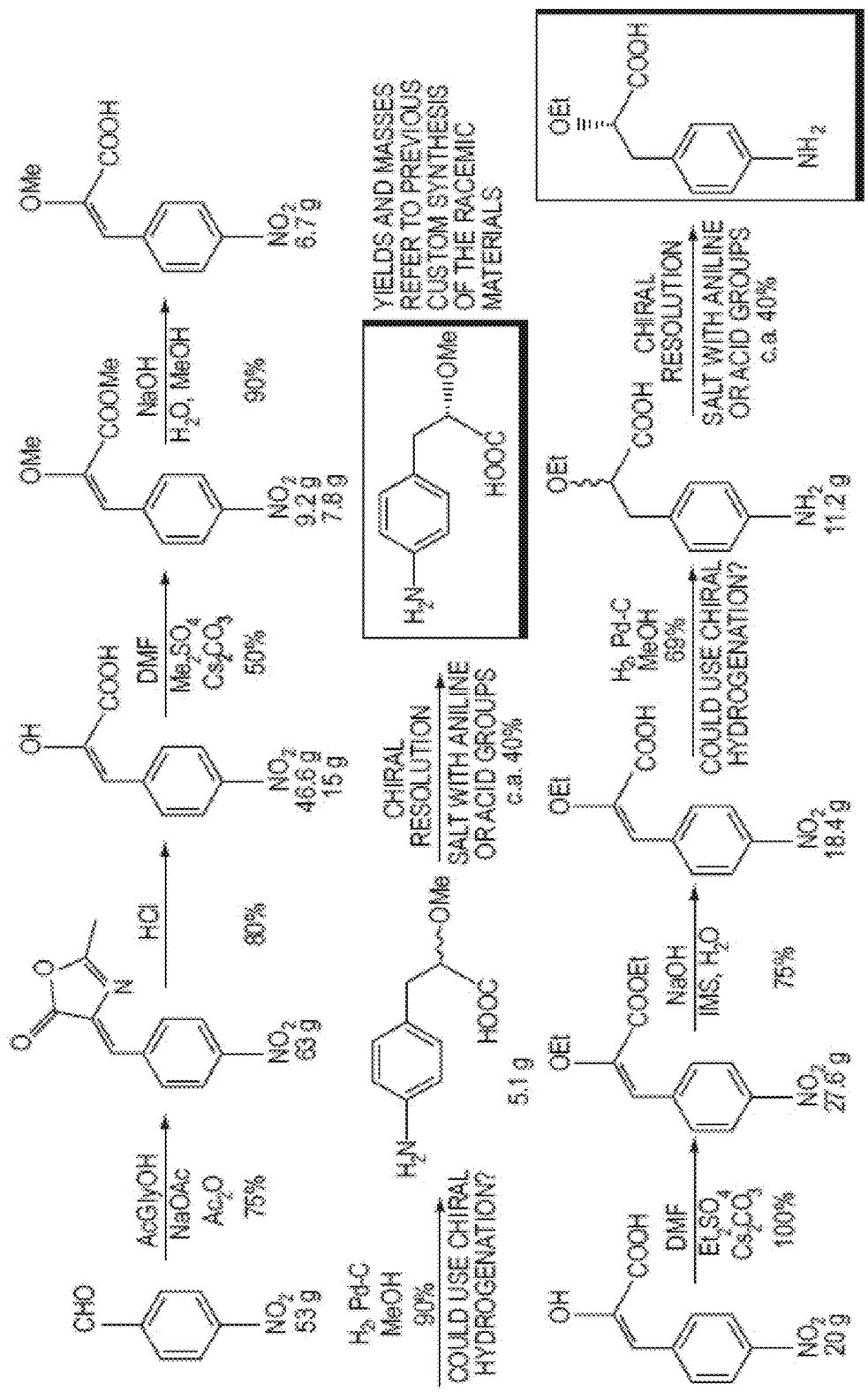
FIG. 12A: SYNTHETIC AND SUBSEQUENT ENANTIOMERIC RESOLUTION SCHEME FOR COMPOUND 32

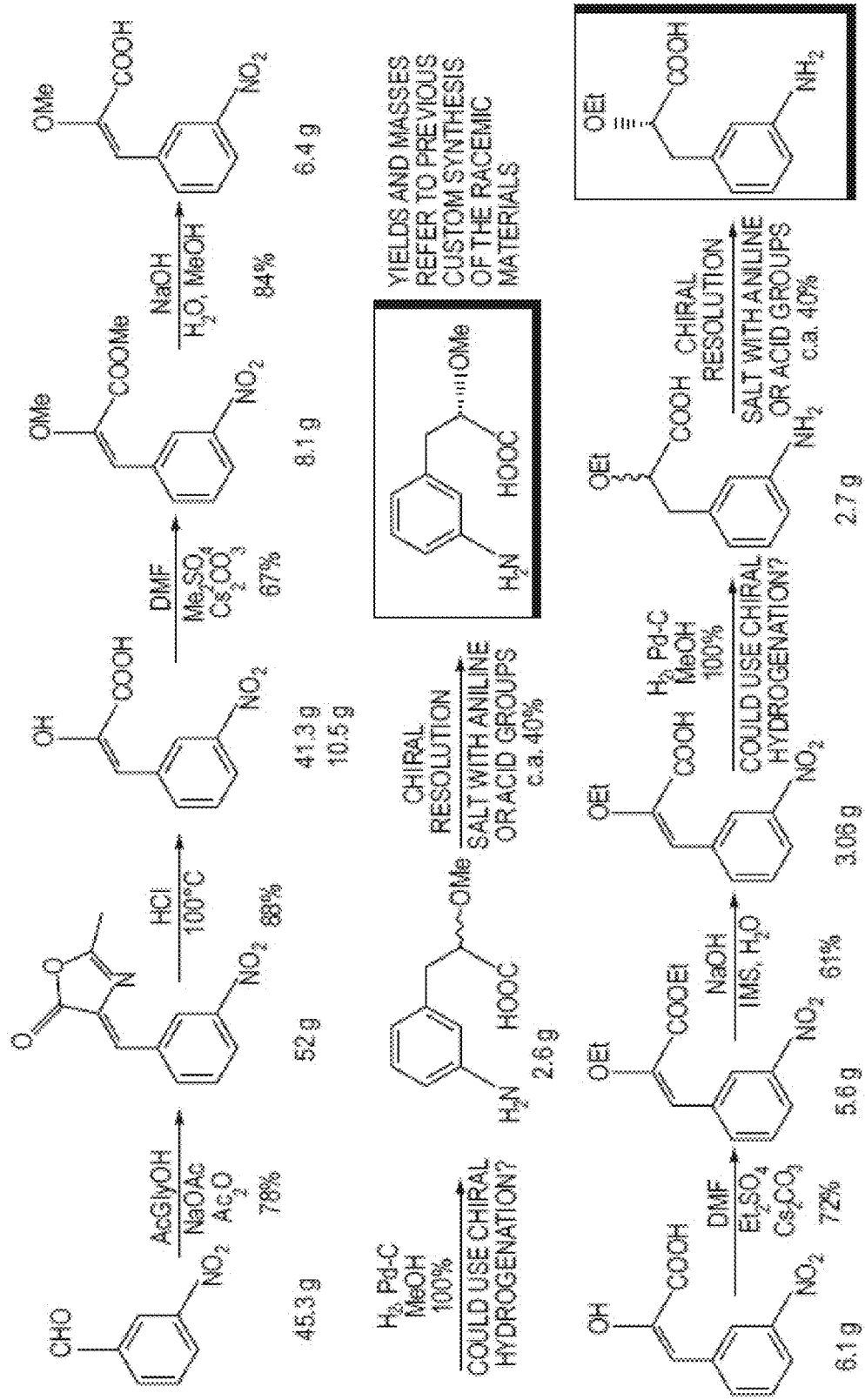
FIG. 12B : SYNTHETIC AND SUBSEQUENT ENANTIOMERIC RESOLUTION SCHEME FOR COMPOUND 32

COMPOUNDS AND THEIR SALTS SPECIFIC TO THE PPAR RECEPTORS AND THE EGF RECEPTORS AND THEIR USE IN THE MEDICAL FIELD

CROSS-REFERENCE TO RELATED APPLICATIONS

This application is a continuation of U.S. application Ser. No. 14/671,579, filed Mar. 27, 2015, which is a divisional of U.S. application Ser. No. 14/202,386, filed Mar. 10, 2014 (issued as U.S. Pat. No. 9,133,099), which is a continuation of U.S. application Ser. No. 13/408,439, filed Feb. 29, 2012 (issued as U.S. Pat. No. 8,710,100), which is a divisional of U.S. application Ser. No. 11/989,090, filed Jun. 6, 2008 (issued as U.S. Pat. No. 8,153,841), which is the national phase of International (PCT) Application No. PCT/IE2006/000078, filed Jul. 24, 2006, which claims the benefit of and priority to Italian Patent Application No. RM2005 A 000389, filed Jul. 22, 2005, the entire disclosure of each of which is incorporated by reference herein.

FIELD OF THE INVENTION

The present invention relates to compounds and their salts specific to the PPAR receptors and the EGF receptors and their use in the medical field.

OBJECT OF THE INVENTION

In particular, the compounds and their salts according to the present invention can be used advantageously for the prevention and treatment of tumours expressing the PPARγ receptors (Peroxisome Proliferator-Activated Receptors) and the EGF receptors (Epidermal Growth Factor receptors) such as tumours of the: oesophagus, stomach, pancreas, colon, prostate, breast, uterus and appendages, kidneys and lungs. Moreover, the compounds and their salts according to the invention can be used for the treatment of chronic inflammatory diseases, in particular chronic intestinal diseases, such as Crohn's disease and ulcerative rectocolitis.

BACKGROUND TO THE INVENTION

The PPARγ receptors are nuclear receptors (group of approx. 50 transcription factors) which control the expression of many genes that are important for the regulation of lipid metabolism, the synthesis of insulin and the processes of carcinogenesis and inflammation. (Bull A W, Arch Pathol Lab Med 2003; 127: 1121-1123) (Koeffler H P, Clin Cancer Res 2003; 9: 1-9) (Youssef J et al., J Biomed Biotec 2004; 3: 156-166).

There are various natural and synthetic agonists which bind to the PPARγ receptors and alter their conformation, giving rise to activation. Natural and synthetic ligands are described in The Lancet 2002; 360:1410-1418.

Recent studies have shown that treatment of tumour cells with ligands of the PPARγ receptors induces a decrease in cellular proliferation, cell differentiation and apoptosis, suggesting potential application of such compounds as agents for preventing carcinogenesis (Osawa E et al., Gastroenterology 2003; 124:361-367).

Other studies have shown that ligands of the PPARγ receptors (e.g. troglitazone) have anti-inflammatory effects and inhibit the mucosal inflammatory response in animal models of IBD (Tanaka T at al., Cancer Res 2001; 61: 2424-2428).

Moreover, evidence has been published very recently that the intestinal anti-inflammatory activity of 5-ASA, the gold standard in the treatment of IBD, is dependent on binding, and consequent activation, of the PPARγ receptors (Rousseaux C at al., J Exp Med 2005; 201: 1205-1215).

The transmembrane receptor with tyrosine-kinase EGF activity is expressed to a very high degree in activated form in various types of neoplasms (Mendelsohn J, Endocr Relat Cancer 2001; 8: 3-9) (Harari P M, Endocr Relat Cancer 2004; 11: 689-708).

Overexpression of the receptor is also related to potential ability of carcinomatous cells to metastasize. In connection to this, it has been demonstrated that EGF promotes the migration and invasiveness of various cell types connected with lesions at the level of interactions with the extracellular matrix (Brunton et al., Oncogene 1997; 14: 283-293).

Numerous studies performed both on experimental animals and in humans have established the efficacy of inhibitors of the EGF receptor in controlling proliferation and the spread of tumours (Mendelsohn J, Endocr Relat Cancer 2001; 8: 3-9) (Harari P M, Endocr Relat Cancer 2004; 11: 689-708).

There is no doubt that the intracellular signals triggered by activation of the EGF receptor facilitate the growth and survival of neoplastic cells, contributing to the development of the pathology, and that such signals are essential in determining the ability of tumour cells to spread and colonize remote organs.—(Mendelsohn J. Endocr Relat Cancer 2001; 8: 3-9) (Kari C et al., Cancer Res 2003; 63: 1-5).

From the foregoing and bearing in mind, moreover, that from the biological standpoint, chronic inflammatory processes play a part in carcinogenesis, it becomes clear that there is a real need for innovative research into new chemical entities which, by their complementary action both on the PPARγ receptors and on the EGF receptors, are able to exert anti-inflammatory and anti-tumour action, of the chemo-preventive, anti-proliferative and anti-metastatic type.

The present invention provides a novel class of compounds that are suitable for the prevention and treatment of cancer and of chronic inflammation by the modulation of specific receptors such as the PPARγ receptors and the EGF receptors.

SUMMARY OF THE INVENTION

The present invention relates to novel and inventive medical and therapeutic uses of a series of compounds in so far as any of these compounds are not known, the invention also relates to these compounds.

The present invention relates to compounds comprising the general formula (I)

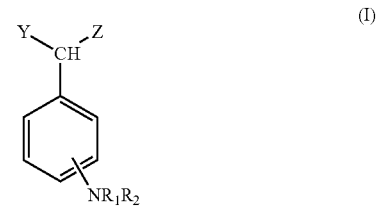

in which $R_1$ and $R_2$, which may be identical or different, are selected from the group comprising —H or a linear or branched alkyl group having from 1 to 6 carbon atoms or together form an aromatic or aliphatic ring with 5 or 6 atoms;

Y and Z, which may be identical or different, are selected from the group comprising —H, —OH, —COOH, —OR$_3$, —CH(OR$_3$)COOH, in which R$_3$ is selected from H, phenyl, benzyl, —CF, or —CF$_2$CF$_3$, vinyl, allyl and a linear or branched alkyl group having from 1 to 6 carbon atoms.

The present invention also relates to a subgroup of compounds, of general formula (Ia)

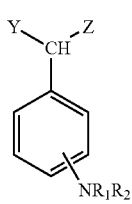

in which

R$_1$ and R$_2$, which may be identical or different, are selected from the group comprising —H or a linear or branched alkyl group having from 1 to 6 carbon atoms Y and Z, which may be identical or different, are selected from the group comprising —H, —OH, —COOH, —OR$_2$, —CH(OR$_3$)COOH, in which R$_3$ is selected from —H and a linear or branched alkyl group having from 1 to 6 carbon atoms.

In some embodiments of the Invention, Z and Y are different. In some embodiments of the invention, at least one of Y or Z terminates in —COOH. Therefore, in some embodiments of the invention, Y or Z (and in some embodiments at least one of Y or Z, and in some embodiments, only one of Y or Z) is —COOH. In some embodiments of the invention, Y or Z (and in some embodiments at least one of Y or Z, and in some embodiments, only one of Y or Z) is —CH(OR$_3$)COOH.

The present invention also relates to compounds according to both formula (I) and (Ia), except wherein Y and Z, which may be identical or different, are selected from the group comprising —H, —COOH, —OR$_3$, —CH(OR$_3$)COOH. Therefore, in some embodiments of the invention, Z or Y may not be —OH. In such embodiments of the invention, compounds 10 and 11 are excluded.

In some embodiments of the invention, when Y is —H and Z is —CH(OH)COOH, the group NR$_1$R$_2$ is connected at the 3' position. Thus, in some embodiments of the invention, compound 21 is excluded:

In other embodiments of the invention, when Z is —OCH$_3$ and Y is —COOH, the group NR$_1$R$_2$ is connected at the 4' position. Thus, in some embodiments of the invention, the compound 22 is excluded.

In some embodiments of the invention, when Y is —H and Z is —CH(OCH$_3$)COOH, the group NR$_1$R$_2$ is connected at the 4' position. Thus, in some embodiments of the invention, compound 35 is excluded:

In particular, the aforementioned linear or branched alkyl group having from 1 to 6 carbon atoms can be selected from —CH$_3$, —CH$_2$CH$_3$, —CH(CH$_3$)$_2$, —CH$_2$CH$_2$CH$_3$, —C$_n$H$_{2n-1}$.

The compounds of formula (I) and (Ia) can be selected from the group comprising
3-(3'-aminophenyl)2-hydroxypropanoic acid (compound 20)
2-(4-aminophenyl)2-methoxyacetic acid (compound 23)
2-(3-aminophenyl)2-ethoxyacetic acid (compound 32)
2-(4-aminophenyl)2-ethoxyacetic acid (compound 33)
3-(4'-aminophenyl)2-methoxypropionic acid (compound 34)
3-(4'-aminophenyl)2-ethoxypropionic acid (compound 39)
3-(3'-aminophenyl)2-ethoxypropionic acid (compound 40).

The above compound names can also be written in standard chemical nomenclature as follows (which nomenclature will be used throughout the text):
(±)-2-hydroxy-3-(3'-aminophenyl) propionic acid (compound 20)
(±)-2-methoxy-2-(4'-aminophenyl) acetic acid (compound 23)
(±)-2-ethoxy-2-(3'-aminophenyl) acetic acid (compound 32)
(±)-2-ethoxy-2-(4'-aminophenyl) acetic acid (compound 33)
(±)-2-methoxy-3-(4'-aminophenyl) propionic acid (compound 34)
(±)-2-ethoxy-3-(4'-aminophenyl) propionic acid (compound 39)
(±)-2-ethoxy-3-(3'-aminophenyl) propionic acid (compound 40).

The compounds according to the present invention cart be used advantageously in the medical field. Therefore the present invention relates to a pharmaceutical composition comprising one or more compounds as defined above as active principles in combination with one or more pharmaceutically acceptable excipients or adjuvants.

The present invention relates, moreover, to the use of the compounds as defined above for the preparation of a medicinal product for the prevention and treatment of tumours expressing the PPARγ receptors and the EGF receptors such as, for example, tumour of the oesophagus, stomach, pancreas, colon, prostate, breast, of the uterus and its appendages, of the kidneys and of the lungs.

Moreover, the invention relates to the use of the compounds according to the invention for the preparation of a medicinal product for the treatment of chronic inflammatory diseases such as, for example, Crohn's disease and ulcerative rectocolitis.

In particular, the compounds according to the invention that can be used in the aforementioned applications, apart from those already described, can be as follows:
(R,S)-2-hydroxy-2-(3-aminophenyl)acetic acid (compound 10)
(R,S)-2-hydroxy-2-(4-aminophenyl)acetic acid (compound 11)
(R,S)-2-hydroxy-3-(4'-aminophenyl)propionic acid (compound 21)
(R,S)-2-methoxy-3-(3'-aminophenyl)propionic acid (compound 35)
(R,S)-2-methoxy-3-(3-aminophenyl)propionic acid (compound 34).

The above compound names can also be written in standard chemical nomenclature as follows (which nomenclature will be used throughout the text):
(±)-2-hydroxy-2-(3'-aminophenyl)acetic acid (compound 10)
(±)-2-hydroxy-2-(4'-aminophenyl)acetic acid (compound 11)
(±)-2-hydroxy-3-(4'-aminophenyl)propionic acid (compound 21)
(±)-2-methoxy-3-(3'-aminophenyl)propionic acid (compound 35)
(±)-2-methoxy-3-(4'-aminophenyl)propionic acid (compound 34).

According to one embodiment, $R_3$ of the compounds of formula (I) can be H according to the following formula (II)

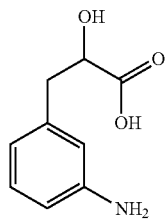

(II)

while $R_1$, $R_2$, X and Y are defined above.

According to another embodiment, $R_3$ of the compounds of formula (I) can be —$CH_3$ according to the following formula (III)

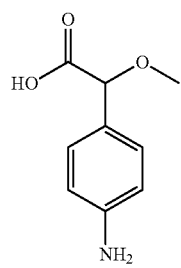

(III)

while $R_1$, $R_2$, X and Y are defined above.

According to another embodiment, $R_3$ of the compounds of formula (I) can be —$CH_2CH_3$ according to the following formula (IV)

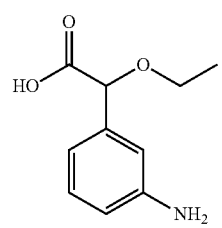

(IV)

while $R_1$, $R_2$, X and Y are defined above.

According to another embodiment, $R_3$ of the compounds of formula (I) can be —$CH_2CH_3$ according to the following formula (V)

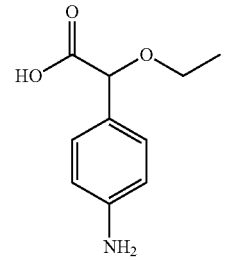

(V)

while $R_1$, $R_2$, X and Y are defined above.

According to another embodiment, $R_3$ of the compounds of formula (I) can be —$CH_3$ according to the following formula (VI)

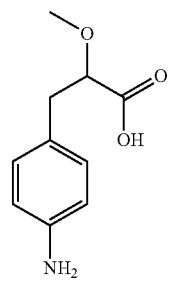

(VI)

while $R_1$, $R_2$, X and Y are defined above.

According to another embodiment, $R_3$ of the compounds of formula (I) can be —$CH_3$ according to the following formula (VI)

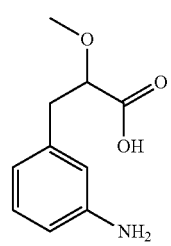

(VI)

while $R_1$, $R_2$, X and Y are defined above.

According to another embodiment, $R_3$ of the compounds of formula (I) can be —$CH_2CH_3$ according to the following formula (VII)

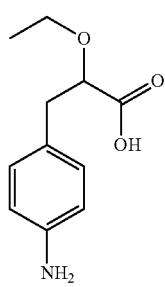

(VII)

while $R_1$, $R_2$, X and Y are defined above.

According to another embodiment, $R_3$ of the compounds of formula (I) can be —$CH_2CH_3$ according to the following formula (VIII)

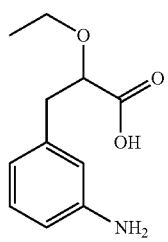

(VIII)

while $R_1$, $R_2$, X and Y are defined above.

According to another embodiment, $R_3$ of the compounds of formula (I) can be —$CH_3$ according to the following formula (IX)

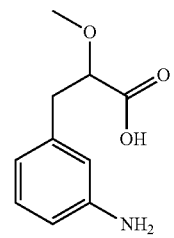

(IX)

while $R_1$, $R_2$, X and Y are defined above.

Preferably, the compounds of formula (I) can be selected from the group comprising
(±)-2-hydroxy-3-(3'-aminophenyl) propionic acid (compound 20)
(±)-2-methoxy-2-(4'-aminophenyl) acetic acid (compound 23)
(±)-2-ethoxy-2-(3'-aminophenyl) acetic acid (compound 32)
(±)-2-ethoxy-2-(4'-aminophenyl) acetic acid (compound 33)
(±)-2-methoxy-3-(4'-aminophenyl) propionic acid (compound 34)
(±)-2-ethoxy-3-(4'-aminophenyl) propionic acid (compound 39)
(±)-2-ethoxy-3-(3'-aminophenyl) propionic acid (compound 40).

The compounds according to the present invention can be used advantageously in the medical field. Therefore the present invention relates to a pharmaceutical composition comprising one or more compounds as defined above as active principles in combination with one or more pharmaceutically acceptable excipients or adjuvants.

The present invention relates, moreover, to the use of the compounds as defined above for the preparation of a medicinal product for the prevention and treatment of tumours expressing the PPARγ receptors and the EGF receptors such as, for example, tumour of the oesophagus, stomach, pancreas, colon, prostate, breast, of the uterus and its appendages, of the kidneys and of the lungs.

Moreover, the invention relates to the use of the compounds according to the invention for the preparation of a medicinal product for the treatment of chronic inflammatory diseases such as, for example, Crohn's disease and ulcerative rectocolitis. The present invention also relates to methods of treatment of humans and/or mammals (including rodents, farm animals, domestic pets, mice, rats, hamsters, rabbits, dogs, cats, pigs, sheep, cows, horses).

In particular, the compounds according to the Invention that can be used in the aforementioned applications, apart from those already described, can be as follows:
(±)-2-hydroxy-2-(3-aminophenyl)acetic acid (compound 10)
(±)-2-hydroxy-2-(4-aminophenyl)acetic acid (compound 11)
(±)-2-hydroxy-3-(4'-aminophenyl)propionic acid (compound 21)
(±)-2-methoxy-3-(3'-aminophenyl)propionic acid (compound 35)
(±)-2-methoxy-3-(4'-aminophenyl)propionic acid. (compound 34)

The uses of the compounds described is not restricted to their use in the racemic form. This invention extends to the use of any described compounds in the enantiomerically pure R or S forms, or any mixture in which one enantiomer is in excess of the other, in any proportion.

In fact, docking studies performed Indicate that the S enantiomer to be more active than the R enantiomer, although the pure R enantiomer does show activity.

The molecules of the present invention were derived from molecular modeling work using mesalazine as a basis and all chemically feasible variations were evaluated in order to achieve the best score (affinity and activation of the receptor) in computer docking experiments. Consequently, it is believed that the compounds of the present invention that show comparable function and/or activity to mesalazine do so through similar biological pathways. It is believed that similar characteristics to mesalazine inherent in the molecules of the invention confer upon the molecules a similar activity in relation to the EGF pathway.

The examples provided herein are useful models for use in the prediction of the use of the compounds in the various medical fields already discussed. The models therefore provide valuable and meaningful results regardless of their mechanism of action.

In addition to the above mentioned compounds, the present invention provides for the use of the following compounds:

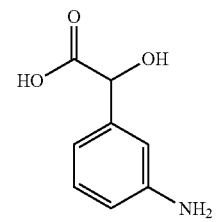

2_10

(R,S) 2″-hydroxy-2-(3-aminophenyl) acetic acid

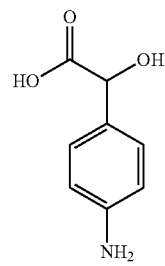

2_11

(R,S) 2″-hydroxy-2-(4-aminophenyl) acetic acid

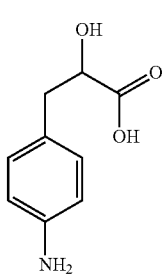

(R,S) 2-hydroxy-3-(4'-aminophenyl)
propionic acid

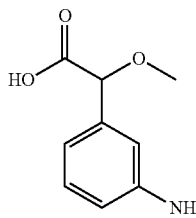

(R,S) 2-methoxy-2-(3-aminophenyl)
acetic acid

The present invention will now be described for purposes of illustration, but without limiting it, according to its preferred embodiments, with particular reference to the diagrams in the appended drawings.

BRIEF DESCRIPTION OF THE DRAWINGS AND TABLE

Table 1. Percentages of DLD-1 cell inhibition by graded doses (0.5-10 mM) of the specified compounds. Cells were cultured in the presence or absence of the compounds, and cell growth was then assessed by the colormetric (BrdU) assay after 48 hours culture.

FIG. 1 shows the structures of compounds 20, 23, 32, 33, 34, 35, 39 and 40.

Figure 2:
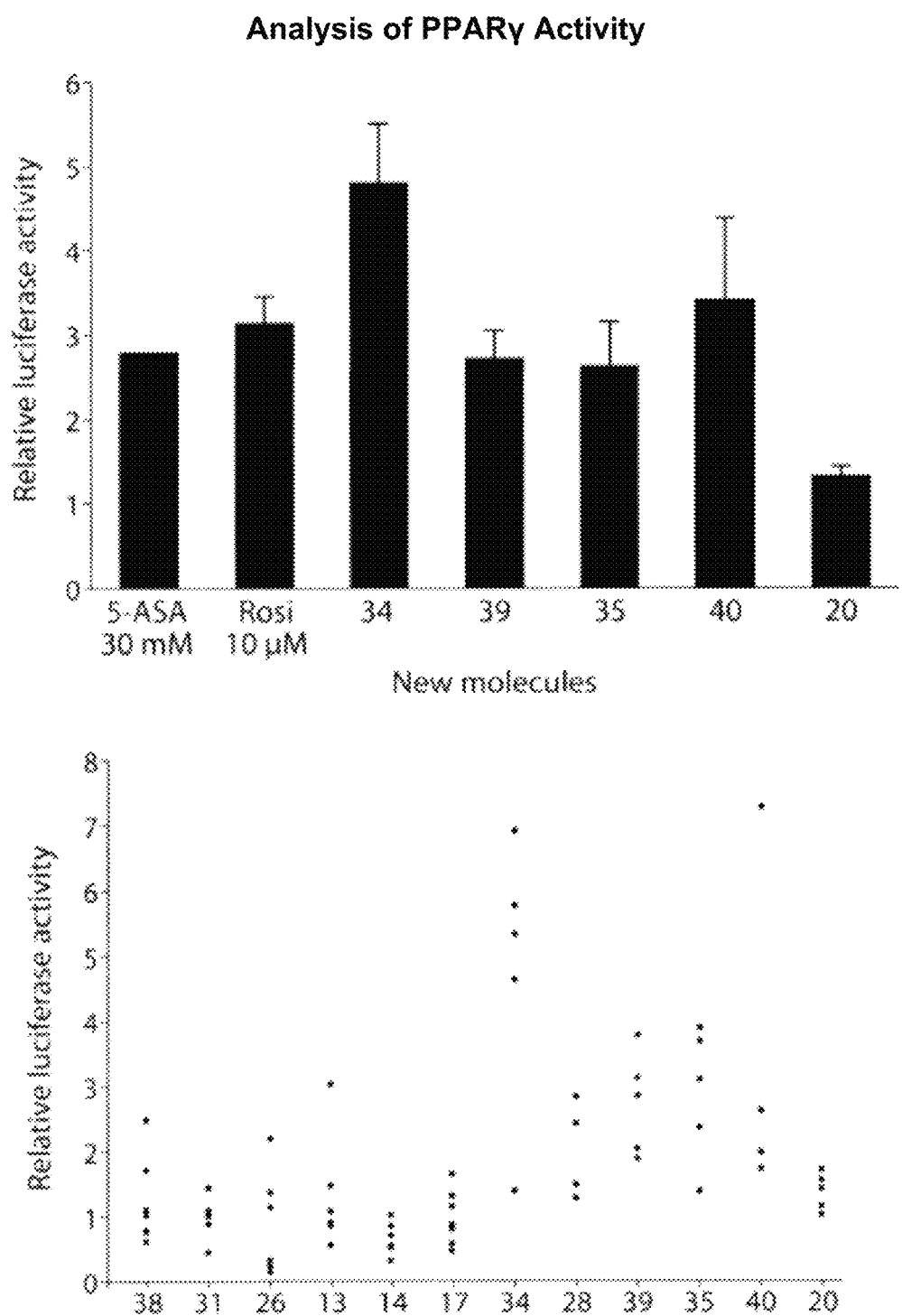

FIG. 2: PPARγ activity by treatment with compounds.

Figure 3:
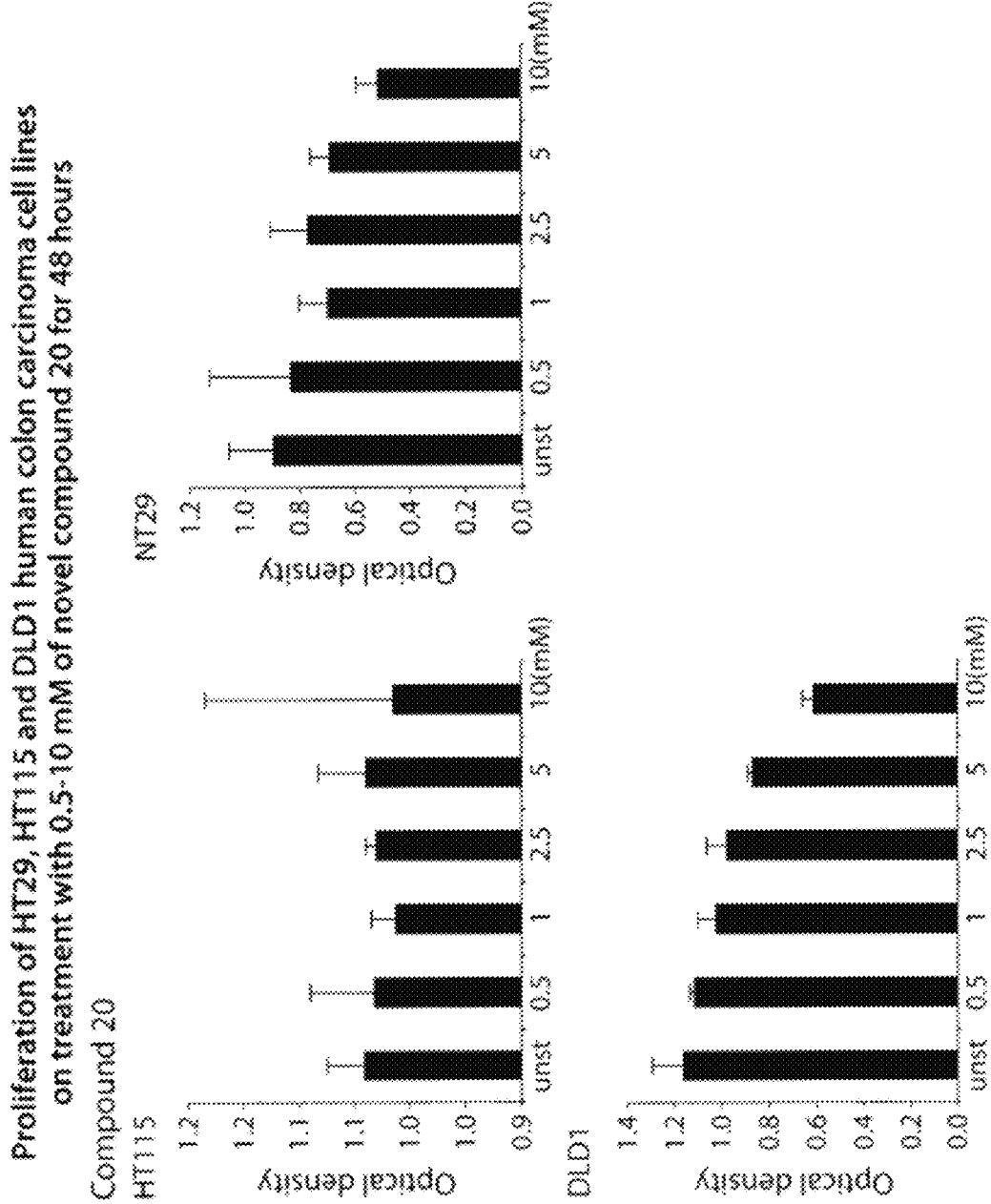
Figure 4:
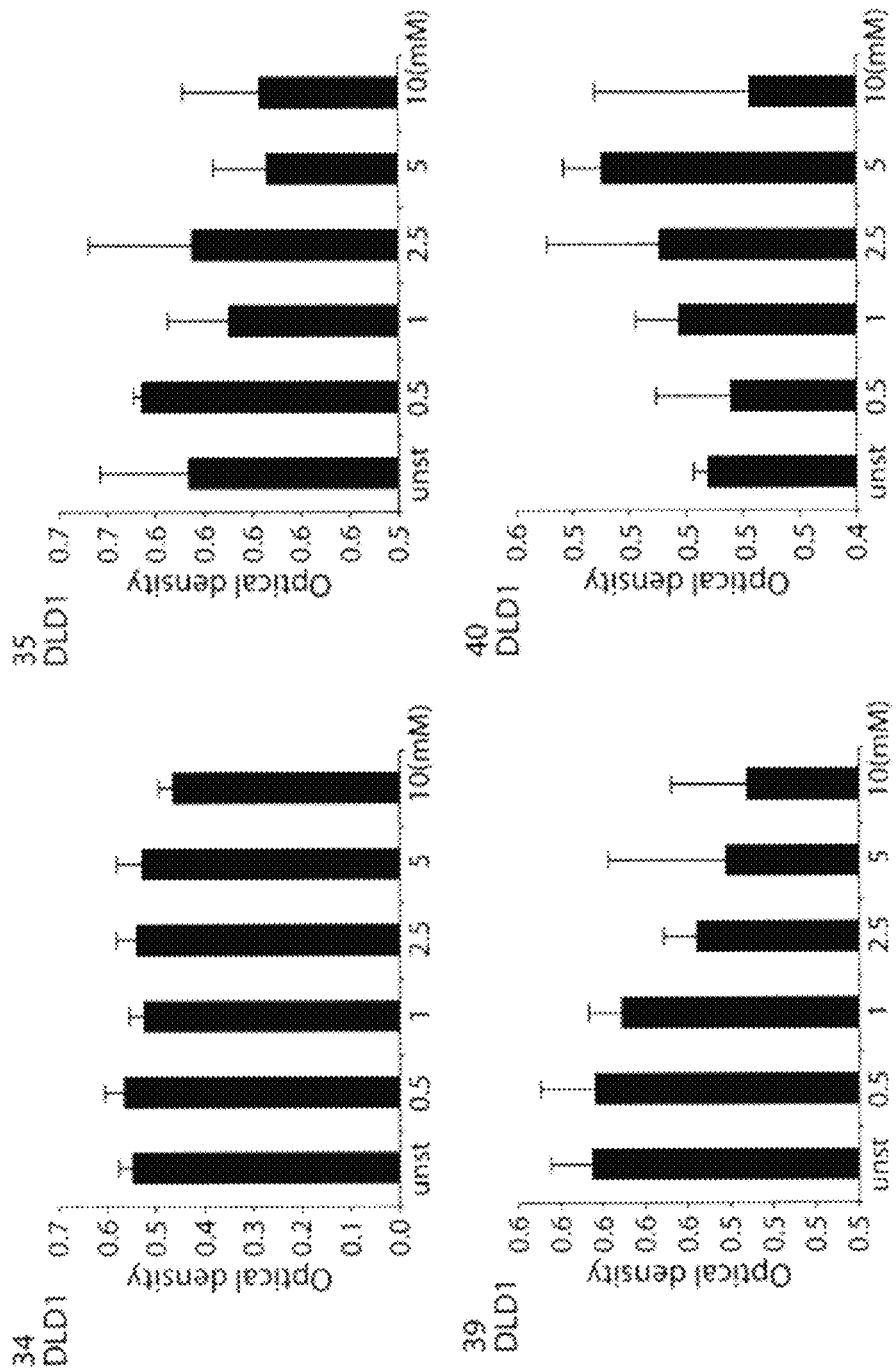

FIG. 3 and FIG. 4: Effect of the specified substances on the proliferation of human colon carcinoma cell lines (i.e. HT29, HT115 and DLD1). Cells were treated with increasing concentrations of substances (0.5-10 mM)) for 48 hours and the proliferation was determined by using a colorimetric assay for the measurement of BrdU Incorporation. Optical density (OD) was determined at 450 nm using an ELISA reader. Data indicate the mean±SD of 3 separate experiments.

FIG. 5: Docking of (R) Compound 34 to PPARγ receptor (amino acid residues labeling and hydrogen bonding is shown).

FIG. 6: Docking of (S) Compound 34 to PPARγ receptor (amino acid residues labeling and hydrogen bonding is shown).

FIG. 7: Docking of (R) Compound 35 to PPARγ receptor (amino acid residues labeling and hydrogen bonding is shown).

FIG. 8: Docking of (S) Compound 35 to PPARγ receptor (amino acid residues labeling and hydrogen bonding is shown).

FIG. 9: Docking of (R) Compound 39 to PPARγ receptor (amino acid residues labeling and hydrogen bonding is shown)

FIG. 10: Docking of (S) Compound 39 to PPARγ receptor (amino acid residues labeling and hydrogen bonding is shown).

FIG. 11: Docking of mesalamine to PPARγ receptor (amino acid residues labeling and hydrogen bonding is shown).

FIG. 12A and FIG. 12B: Schematic Synthesis and Subsequent Resolution of Compound 39.

EXAMPLE 1

Method of Preparing (±)-2-hydroxy-3-(3'-aminophenyl)-propanoic Acid (Compound 20)

Step 1

3-Nitrobenzaldehyde (45.3 g, 0.3 mol), N-acetylglycine (42.1 g, 0.36 mol) and sodium acetate (32 g, 0.39 mol) were mixed with acetic anhydride (142 ml, 1.5 mol) and the resulting mixture heated with stirring to 120° C. for 6 hrs, giving a dark solution. The mixture was then cooled to RT overnight, resulting in the formation of a precipitated solid. The reaction mixture was poured into ice-water (130 g) and the resulting suspended solid was collected by filtration. The crude solid product (72 g) was washed with acetone (80 ml) then recrystallized from hot acetone (320 ml) to give a crystalline solid that was washed with 50% aqueous ethanol, then dried at 40° C./40 mmHg to give 2-methyl-4-(3-nitrobenzylidene)oxazol-5(4H)-one (49.0 g, 78%) as pale yellow needles. $^1$H NMR (δ, 250 MHz, CDCl$_3$)=2.47 (3H, s), 7.15 (1H, s), 7.63 (1H, dd, 8.2 & 7.6 Hz), 8.27 (1H, d, 8.2 Hz), 8.34 (1H, d, 7.6 Hz), 9.02 (1H, s).

Step 2

2-Methyl-4-(3-nitrobenzylidene)oxazol-5(4H)-one (52.0 g, 0.224 mol) was mixed with 3M hydrochloric acid (1.3 L) and the suspension stirred at 100° C. for 6 h. The resulting suspension was stirred at RT overnight then the suspended solid was collected by filtration, washed with water (2×40 ml), then dried in vacuo to give 2-hydroxy-3-(3-nitrophenyl) acrylic acid (29.39). The combined filtrate and washes were extracted with ethyl acetate (4×0.5 L), then the combined organic extracts were dried over sodium sulfate and concentrated to dryness to give a further crop of 2-hydroxy-3-(3-nitrophenyl)acrylic acid (12.0 g). The total yield of 2-hydroxy-3-(3-nitrophenyl)acrylic acid was 41.3 g (88%), $^1$H NMR (δ, 250 MHz, DMSO-$d_6$)=6.56 (1H, s), 7.64 (1H, t, 8 Hz), 8.0-8.1 (2H, m), 8.78 (1H, s), 9.95 (1H, brs), 12.80 (1H, brs).

Step 3

Sodium ethoxide (1.8 g, 26.4 mmol) was added portionwise at 0° C. to a stirred solution of 2-hydroxy-3-(3-nitrophenyl)acrylic acid (5.25 g, 25.0 mmol) in methanol (131 ml) to form a clear, pale yellow solution. Sodium borohydride (1 g, 26.4 mmol) was then carefully added in two portions and the mixture stirred at 5-10° C. for 30 mins. A small amount of water was then added to quench the reaction and destroy any excess NaBH$_4$. The methanol was removed in vacuo to give a solid residue, which was ground with a 5:2 mixture of ethyl acetate and heptane (21 ml) then further ground with 3% aqueous methanol. The resulting solid was collected by filtration and dried in vacuo to give 2-hydroxy-3-(3-nitrophenyl)propionic acid (3.0 g, 57%).

$^1$H NMR (δ, 250 MHz, DMSO-$d_6$)=2.97 (1H, dd, 14 & 8.2 Hz), 3.15 (1H, dd, 14 & 4.2 Hz), 4.23 (1H, dd, 8.2 & 4.2 Hz), 7.58 (1H, t, 8 Hz), 7.70 (1H, d, 8 Hz), 8.0-8.15 (2H, m).

Step 4

A mixture of 2-hydroxy-3-(3-nitrophenyl)propionic acid (3.0 g, 14.2 mmol), methanol (129 ml) and 5% palladium on activated charcoal (600 mg, 2 mol %) was hydrogenated at 10 psi H$_2$ atmosphere for 1 hr. The mixture was then filtered through celite, the filter cake was washed with methanol and the filtrates concentrated at 40° C. under high vacuum to give the product as a foamy solid. This was dissolved in water and the solution freeze-dried to give (±)-2-hydroxy-3-(3'-aminophenyl)-propanoic acid (2.6 g, 100%) as a white solid.

$^1$H NMR (δ, 250 MHz, DMSO-$d_6$)=2.61 (1H, dd, 13.6 & 8.3 Hz), 2.81 (1H, dd, 13.6 & 4.6 Hz), 4.09 (1H, dd, 8.25 & 4.6 Hz), 6.35-6.43 (2H, m), 6.45 (1H, d, 1 Hz), 6.90 (1H, t, 7.6 Hz).

EXAMPLE 2

Method of Preparing (±)-2-methoxy-2-(4'-aminophenyl)-acetic Acid (Compound 23)

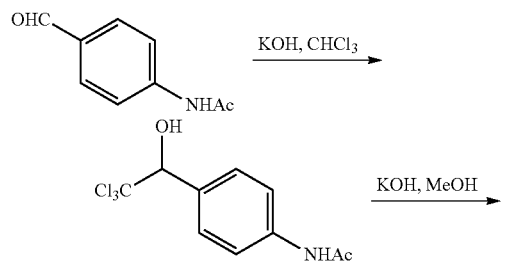

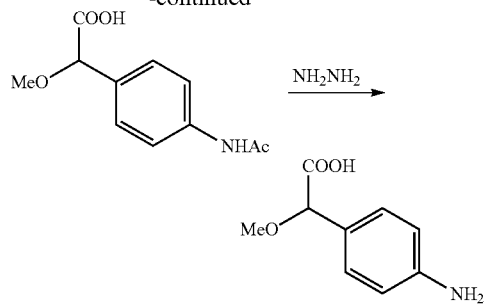

Step 1

A solution of potassium hydroxide (6.72 g, 0.12 mol) in methanol (25 ml) was added to a cooled (−7° C.) solution of 4-acetamidobenzaldehyde (24.5 g, 0.15 mol) and chloroform (40.1 g, 0.33 moL) in DMF (100 ml) at such a rate as to keep the temperature below 5° C. The mixture was allowed to warm to 2° C. over 5.5 h then it was added to a mixture of 1M aq. HCl (200 ml) and toluene (200 ml) and stirred overnight. The resulting 2-(4-acetamidophenyl)-trichlorocarbinol was collected by filtration (29 g) and suction dried.

Step 2

Solutions of 2-(4-acetamidophenyl)-trichlorocarbinol (14.0 g, 49.5 mmol) in methanol (330 ml) and potassium hydroxide (13.8 g, 250 mmol) in methanol (150 ml) were combined and the mixture heated to 70-80° C. for 3 hr. After cooling, the KCl by-product was removed by filtration then concentration of the filtrate in vacuo gave 2-(4-acetamidophenyl)-2-methoxyacetic acid (14 g) as a white solid.

Step 3

2-(4-Acetamidophenyl)-2-methoxyacetic acid (7.1 g, 31.8 mmol) was heated with hydrazine monohydrate (40 ml) for 16 hr, cooled and concentrated in vacuo. The resulting residual oil was purified by silica gel column chromatography (eluent 20-40% methanol in CH$_2$Cl$_2$) to give 2.6 g (45%) of (±)-2-methoxy-2-(4'-aminophenyl)-acetic acid $^1$H NMR (δ, 250 MHz, CD$_3$OD): 3.27 (3H, s), 4.43 (1H, s), 6.66 (2H, d, 8.5 Hz), 7.18 (2H, d, 8.2 Hz).

EXAMPLE 3

Method of Preparing (±)-2-ethoxy-2-(3'-aminophenyl)-acetic Acid (Compound 32)

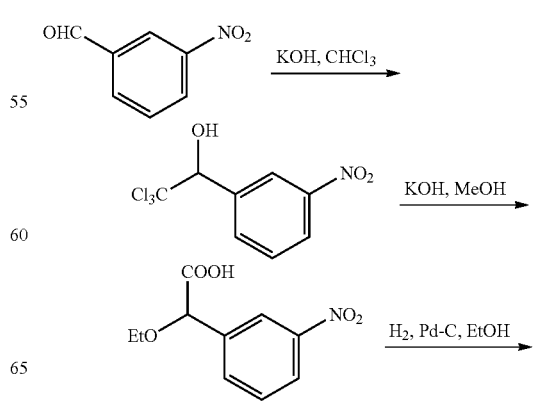

-continued

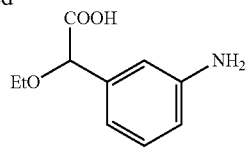

Step 1

3-Nitrobenzaldehyde (25 g, 165 mmol) and chloroform (30 ml, 375 mmol) were dissolved in DMF (100 ml) and the solution cooled to between −5° C. and −10° C. A fresh solution of potassium hydroxide (7.5 g, 134 mmol) in methanol (22.5 ml) was added slowly so as maintain the internal temperature <−5° C. The reaction was maintained at <−5° C. for 2 hr and then quenched with a cooled mixture of aqueous hydrochloric acid (225 ml) in toluene (225 ml). The solution was allowed to warm slowly to room temperature overnight in the ice bath. After this time the toluene layer was separated and the aqueous layer further extracted with toluene. The combined organic layers were washed with water (2×225 ml), 5% sodium bicarbonate solution (225 ml) and water (225 ml). The solution was dried (MgSO$_4$), filtered, and concentrated in vacuo to give 2-(3-nitrophenyl)-trichlorocarbinol as an orange solid (42 g, 155 mmol, 94%).

$^1$H NMR (δ, 250 MHz, CDCl$_3$): 3.7 (br, s, 1H), 5.4 (s, 1H), 7.6 (t, 1H, 8.0 Hz), 8.0 (d, 1H, 8.0 Hz), 8.3 (d, 1H, 8.0 Hz), 8.5 (s, 1H).

Step 2

2-(3-Nitrophenyl)-trichlorocarbinol (20 g, 74 mmol) was dissolved in absolute ethanol (74 ml) and a solution of potassium hydroxide (20.79, 369 mmol) in absolute ethanol (150 ml) was added slowly. The solution was heated at reflux for 4 hr, allowed to cool and then concentrated in vacuo. The residue was acidified with dilute hydrochloric acid and the product extracted in ethyl acetate (×3). The combined organic layers were dried (MgSO$_4$), filtered, and concentrated in vacuo to give 2-ethoxy-2-(3-nitrophenyl)acetic acid as a brown solid (6.4 g, 28.4 mmol, 38%).

$^1$H NMR (δ, 250 MHz, CD$_3$OD): 1.0 (t, 3H, 7.0 Hz), 3.8 (m, 1H), 3.7 (m, 1H), 5.1 (s, 1H), 7.7 (t, 1H, 7.8 Hz), 7.9 (d, 1H, 7.8 Hz), 8.3 (d, 1H, 7.8 Hz), 8.4 (s, 1H).

Step 3

2-Ethoxy-2-(3-nitrophenyl)acetic acid (6.4 g, 28.4 mmol) was dissolved in absolute ethanol (500 ml), 5% palladium on carbon (wet) (1.5 g) added and the mixture hydrogenated at 60 psi overnight. The suspension was filtered through celite and the filtrate concentrated to give (±)-2-ethoxy-2-(3'-aminophenyl)-acetic acid (3.0 g, 15.3 mmol, 54%) as a brown solid.

$^1$H NMR (δ, 250 MHz, CD$_3$OD): 1.2 (t, 3H, J=6.9 Hz), 3.5 (m, 1H), 3.6 (m, 1H), 4.6 (s, 1H), 6.7 (d, 1H, J=7.6 Hz), 6.9 (m, 2H), 7.0 (t, 1H, J=7.6 Hz).

EXAMPLE 4

Method of Preparing (±)-2-ethoxy-2-(4'-aminophenyl)-acetic Acid (Compound 33)

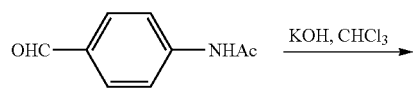

-continued

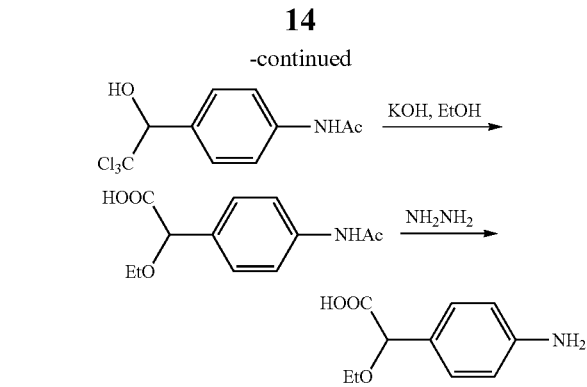

Step 1

See "Compound 23 step 1"

Step 2

Solutions of 2-(4-acetamidophenyl)-trichlorocarbinol (14.0 g, 49.5 mmol) in ethanol (400 ml) and potassium hydroxide (13.8 g, 250 mmol) in ethanol (150 ml) were combined and the mixture heated at 70-80° C. for 2.5 hr. The mixture was cooled, filtered to remove the KCl by-product, and concentrated in vacuo to give 2-(4-acetamidophenyl)-2-ethoxyacetic acid (14 g) as a yellow solid.

Step 3

2-(4-Acetamidophenyl)-2-ethoxyacetic acid (7.54 g, 31.8 mmol) was heated with hydrazine monohydrate (40 ml) for 16 hr, the mixture cooled then concentrated in vacuo. The residual oil was then purified by silica column chromatography (20-40% methanol in CH$_2$Cl$_2$ eluent) to give (±)-2-ethoxy-2-(4'-aminophenyl)-acetic acid (2.3 g, 37%) as a white foam.

$^1$H NMR (δ, 250 MHz, CD$_3$OD): 1.18 (3H, t, 7.0 Hz), 4.42 (1H, qd, 7.3, 2.4 Hz), 4.56 (2H, s), 5.50 (1H, qd, 7.0, 2.1 Hz), 6.66 (2H, d, 8.7 Hz), 7.20 (2H, d, 8.5 Hz)

EXAMPLE 5

Method of Preparing (±)-2-methoxy-3-(4'-aminophenyl)-propionic Acid (Compound 34)

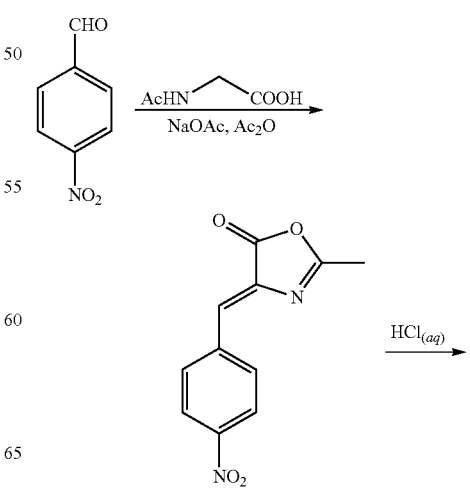

-continued

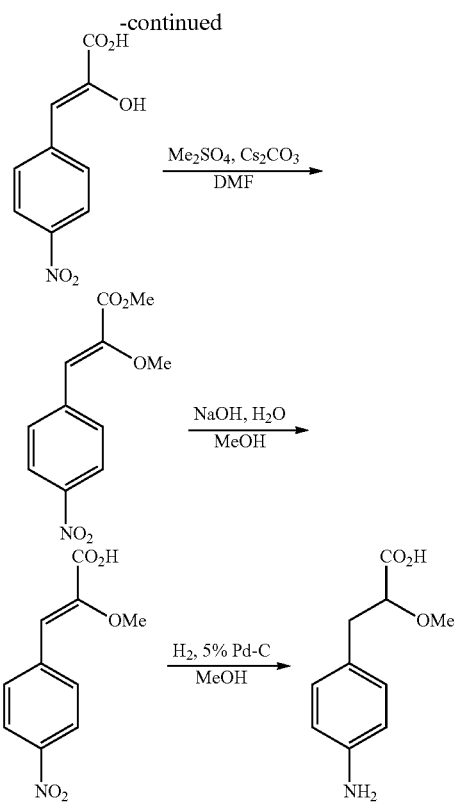

Step 1

4-Nitrobenzaldehyde (53.7 g, 0.356 mol), N-acetylglycine (49.9 g, 0.427 mol) and sodium acetate (37.9 g, 0.463 mol) were mixed with acetic anhydride (168 g, 1.78 mol) and the resulting mixture heated with stirring to 120° C. for 6 hrs, giving a dark suspension. The mixture was then cooled to RT overnight, resulting in the formation of a precipitated solid. The reaction mixture was poured into ice-water (150 g) and the resulting suspended solid was collected by filtration. The crude solid product was washed with acetone (100 ml) then recrystallized from hot acetone (650 ml) to give a crystalline solid that was washed with 50% aqueous ethanol, then dried in vacuo to give 2-methyl-4(4-nitrobenzylidene)oxazol-5(4H)-one (55.0 g, 66%) as pale yellow needles. The crystallisation mother liquors and washes were combined and evaporated to give a solid residue that was recrystallized from acetone to give a second crop of 2-methyl-4-(4-nitrobenzylidene)oxazol-5(4H)-one (8 g, 10%). The combined yield of 2-methyl-4-(4-nitrobenzylidene)oxazol-5(4H)-one was 63 g (76%)

$^1$H NMR ($\delta$, 250 MHz, CDCl$_3$)=2.47 (3H, s), 7.14 (1H, s), 8.28 (4H, m).

Step 2

2-Methyl-4-(4-nitrobenzylidene)oxazol-5(4H)-one (63.0 g, 0.272 mol) was mixed with 3M hydrochloric acid (1.2 L) and the suspension was stirred at 100° C. for 6 h. The resulting suspension was stirred at RT overnight then the suspended solid was collected by filtration, washed with water (2×50 ml), then dried in vacuo to give 2-hydroxy-3-(4-nitrophenyl)acrylic acid (46.6 g, 81%). The combined filtrate and washes were extracted with ethyl acetate (4×0.5 L), then the combined organic extracts were dried over sodium sulfate and concentrated to dryness to get a further crop of 2-hydroxy-3-(4-nitrophenyl)acrylic acid (0.8 g, 1%). The total yield of 2-hydroxy-3-(4-nitrophenyl) acrylic acid was 47.4 g (82%).

$^1$H NMR ($\delta$, 250 MHz, DMSO-d$_6$)=6.52 (1H, s) 8.01 (2H, d, 8.5 Hz), 8.22 (2H, d, 8.5 Hz).

Step 3

A mixture of 2-hydroxy-3-(4-nitrophenyl)acrylic acid (15 g, 71.7 mmol), cesium carbonate (56 g, 172.1 mmol) and dimethyl sulphate (14.2 ml, 150.6 mmol) in DMF (270 ml) was stirred at RT for 18 hr. Water (220 ml) and ethyl acetate (150 ml) were added and the layers separated. The aqueous layer was further extracted with ethyl acetate (4×100 ml) then the combined organics were washed with water (6×100 ml), brine (2×120 ml) and concentrated to half volume. Heptane was added (70 ml) and the mixture concentrated to 200 ml volume. The resulting precipitated solid was collected by filtration, washed with heptane (2×100 ml) and suction dried on the filter to afford methyl 2-methoxy-3-(4-nitrophenyl)acrylate as a tan solid (9.2 g, 54% yield) containing a trace of heptane.

$^1$H NMR ($\delta$, 250 MHz, DMSO-d$_6$): 3.82 (s, 3-H, OMe), 3.84 (s, 3-H, OMe), 7.02 (s, 1-H. CH=), 8.04 (d, 2-H, CHaromatic), 8.26 (d, 2-H, CHaromatic).

Step 4

Methyl 2-methoxy-3-(4-nitrophenyl)acrylate (7.8 g, 32.8 mmol) was dissolved in IMS (156 ml). A solution of NaOH (1.44 g, 36.1 mmol) in water (78 ml) was added and the mixture stirred at ambient temperature (18° C.) for 18 hr. The reaction mixture was acidified with 1M HCl (120 ml) and the resulting precipitated solid was collected by filtration, washed with water (2×100 ml) and partially suction dried on the filter for 30 mins, followed by vacuum oven drying at 18° C. for 18 hr. Thus 2-methoxy-3-(4-nitrophenyl)acrylic acid was afforded as a tan solid containing some water of crystallisation (6.7 g, 91%).

$^1$H NMR ($\delta$, 250 MHz. DMSO-d$_6$): 3.83 (s, 3-H, OMe), 6.97 (s, 1-H, CH=), 8.02 (d, 2-H, CHaromatic), 8.25 (d, 2-H, CHaromatic).

Step 5

2-Methoxy-3-(4-nitrophenyl)acrylic acid (6.7 g, 30 mmol) was taken up in methanol (700 ml) and THF (300 ml) and 10% Pd on C (wet basis) (0.67 g) was added. The mixture was hydrogenated at 45 psi for 43 mins, followed by repeated refills to 45-48 psi every hour for 3 hr and finally 48 psi for 18 hr. The resulting suspension was filtered through GF/F filter paper and the filter residue washed with MeOH (200 ml). The filtrates were concentrated to an off-white solid. The solid was slurried in IMS (75 ml) at 20° C. for 1.5 hr, filtered, and washed with IMS/heptane (1:2) (20 ml) and dried on the filter for 1 hr to afford (±)-2-methoxy-3-(4'-aminophenyl)-propionic acid as an off-white solid (5.1 g, 88% yield)

$^1$H NMR ($\delta$, 250 MHz, DMSO-d$_6$): 2.74 (m, 2-H), 3.23 (s, 3-H, CH), 3.80 (dd, 1-H, CH), 6.47 (d, 2-H, aromatic), 6.87 (d, 2-H, aromatic).

EXAMPLE 6

Method of Preparing (±)-2-methoxy-3-(3'-aminophenyl)-propionic Acid (Compound 35)

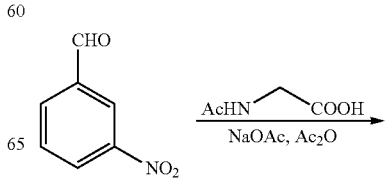

-continued

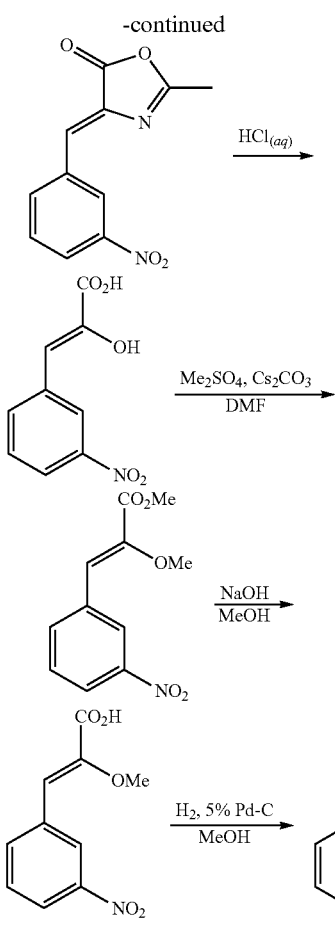

water (3×30 ml) and dried in vacuo at 40° C. to give 2-methoxy-3-(3-nitrophenyl)acrylic acid as a yellow solid (6.4 g, 84%).

$^1$H NMR (δ, 250 MHz, DMSO-$d_6$)=3.82 (3H, s), 7.02 (1H, s), 7.70 (1H, t, 7.93 Hz), 8.10-8.22 (2H, m), 8.65 (1H, s).

Step 5

A mixture of 2-methoxy-3-(3-nitrophenyl)acrylic acid (3.49, 15.25 mmol), methanol (340 ml) and 5% palladium on activated charcoal (1.36 g, 4 mol %) was hydrogenated at 12-36 psi $H_2$ atmosphere for 1.5 hr. The mixture was then filtered through celite, the filter cake washed with methanol and the filtrates concentrated at 40° C. under vacuum to give the product as a foamy solid. This was dissolved in water (100 ml) and the solution freeze-dried to give (±)-2-methoxy-3-(3'-aminophenyl)-propionic acid (2.6 g, 100%) as an off-white solid.

$^1$H NMR (δ, 250 MHz, DMSO-$d_6$)=2.68 (1H, dd, 13.9 & 8 Hz), 2.80 (1H, dd, 13.9 & 4.6 Hz), 3.21 (3H, s), 3.84 (1H, dd, 8.25 & 4.6 Hz), 6.36-6.44 (3H, m), 6.91 (1H, dd, 7.6 Hz).

EXAMPLE 7

Method of Preparing (±)-2-ethoxy 3-(4'-aminophenyl)-propionic Acid (Compound 39). Enantomeric Resolution (FIG. 12A and FIG. 12B)

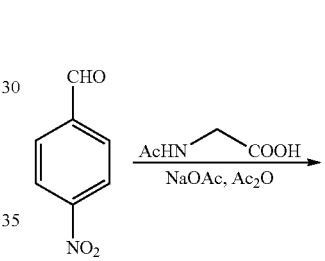

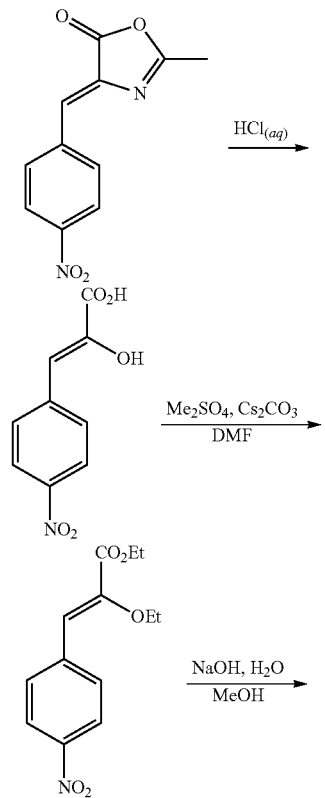

Steps 1 & 2

As per compound 20

Step 3

Dimethyl sulfate (13.23 g, 105 mmol) was added to a stirred mixture of 2-hydroxy-3-(3-nitrophenyl)acrylic acid (10.5 g, 50.0 mmol) and caesium carbonate (39.1 g, 120 mmol) in DMF (105 ml) to form a clear, pale yellow mixture, which was stirred at RT overnight. The resulting dark red suspension was concentrated in vacuo and the residue partitioned between water (100 ml) and dichloromethane (150 ml). The organic layer was separated, further washed with water (2×100 ml), dried over sodium sulphate and filtered through silica gel. The resulting yellow solution was evaporated to dryness in vacuo to give methyl 2-methoxy-3-(3-nitrophenyl)acrylate as a yellow solid (8.1 g, 67%). $^1$H NMR (δ, 250 MHz, DMSO-$d_6$)=3.81 (3H, s), 3.83 (3H, s), 7.08 (1H, s), 7.71 (1H, dd, 7.9 & 8.2 Hz), 8.10-8.22 (2H, m), 8.66 (1H, s).

Step 4

A solution of potassium hydroxide (2.0 g, 35.9 mol) in water (25 ml) was added to a stirred solution of methyl 2-methoxy-3-(3-nitrophenyl)acrylate (8.1 g, 34.2 mmol) in methanol (150 ml) and the resulting mixture was stirred at RT overnight. A further quantity of KOH (0.5 g, 8.9 mmol) in water (10 ml) was added and the mixture heated to 80° C. for 1 hr. The methanol was then evaporated in vacuo and the residue diluted with water (200 ml). The solution was washed with dichloromethane (2×100 ml), filtered through a pad of celite and then acidified by the addition of 3M HCl to pH 3. The mixture was refrigerated for 18 h then the precipitated solid was collected by filtration, washed with

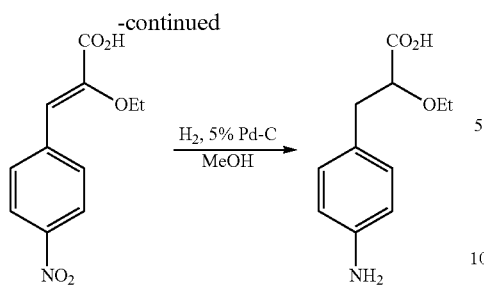

Steps 1 & 2

As per compound 34 steps 1 & 2.

Step 3

2-Hydroxy-3-(4-nitrophenyl)acrylic acid (20 g, 95.6 mmol) was suspended in DMF (200 ml). $Cs_2CO_3$ (74.9 g, 229.9 mmol) and diethyl sulphate (26.3 ml, 201 mmol) were added and dissolution was observed. After stirring for 18 hr at 18° C. water (350 ml) and ethyl acetate (250 ml) were added and the layers separated. The aqueous layer was further extracted with ethyl acetate (5×200 ml) then the combined organics were washed with water (2×200 ml), brine (2×200 ml) and dried over magnesium sulfate. The organics were concentrated to dryness to obtain ethyl 2-ethoxy-3-(4-nitrophenyl)-acrylate as an orange solid containing 3.6% by mass DMF (27.6 g wet, >100% yield). $^1$H NMR (δ, 250 MHz, DMSO-$d_6$): 1.32 (t, 6-H, 2×$CH_2CH_3$), 4.13 (q, 2-H, $CH_2CH_3$), 4.30 (q, 2-H, $CH_2CH_3$), 6.99 (s, 1-H, CH═), 8.06 (d, 2-H, CHaromatic), 8.26 (d, 2-H, CHaromatic).

Step 4

Ethyl 2-ethoxy-3-(4-nitrophenyl)acrylate containing 3.6 wt % DMF (26.07 g corrected, 98.3 mmol) was dissolved in IMS (500 ml) and a solution of NaOH (1.44 g, 36.1 mmol) in water (260 ml) was added. The resulting mixture was stirred at ambient temperature for 18 hr then acidified with 1M HCl (120 ml) and the resulting solid collected by filtration, washed with water (2×100 ml) and suction dried on the filter for 30 mins, followed by vacuum oven drying at 18° C. for 18 hr, 2-Ethoxy-3-(4-nitrophenyl)acrylic acid was thus obtained as an orange solid containing water of crystallisation (18.4 g, 79%).

$^1$H NMR (δ, 250 MHz, DMSO-$d_6$): 1.31 (t, 3-H, Me), 4.11 (q, 2-H, $CH_2$), 6.98 (e, 1-H, CH═), 8.05 (d, 2-H, CHaromatic), 8.25 (d, 2-H, CHaromatic).

Step 5

2-Ethoxy-3-(4-nitrophenyl)acrylic acid (18.4 g wet, approx. 77.5 mmol) was dissolved in MeOH (1.1 L) and 10% Pd on C (wet basis) (1.84 g) was added. The mixture was hydrogenated at 12 psi for 10 mins, followed by repeated refill to 20-28 psi every 10-20 mins for 5 hr then 46 psi for 18 hr. The mixture was filtered through GF/F paper and the residue was slurried in IMS (100 ml), filtered, washed with heptane (100 ml), and suction dried on the filter. Thus (±)-2-ethoxy 3-(4'-Aminophenyl)-propionic acid was obtained as an off-white solid (11.2 g, 69%).

$^1$H NMR (δ, 250 MHz, DMSO-$d_6$): 1.03 (t, 3-H, $CH_3$), 2.73 (m, 2-H,), 3.29 (m, 1H), 3.46 (m, 1H), 3.80 (dd, 1-H), 6.50 (d, 2-H), 6.87 (d, 2-H).

EXAMPLE 8

Method of Preparing (±)-2-ethoxy-3-(3'-aminophenyl)-propanoic Acid (Compound 40)

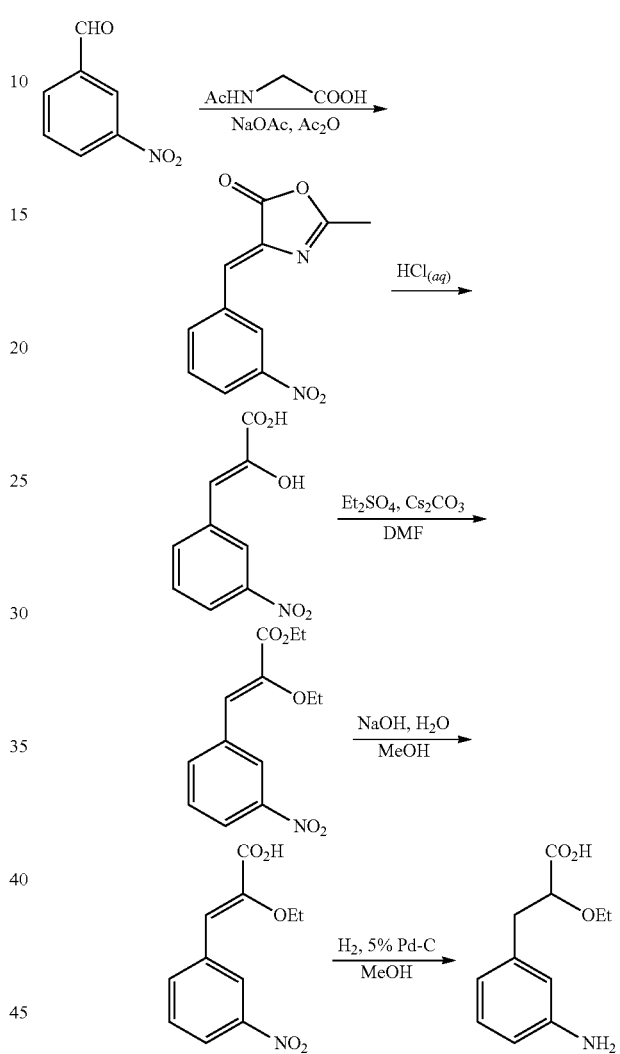

Steps 1 & 2

As per compound 20 steps 1 & 2.

Step 3

Diethyl sulfate (12 g, 78.2 mmol) was added to a stirred mixture of 2-hydroxy-3-(3-nitrophenyl)acrylic acid (6.1 g, 30.0 mmol) and caesium carbonate (29.3 g, 90 mmol) in DMF (61 m) to form a clear, pale yellow mixture, which was stirred at RT overnight. The resulting dark red suspension was heated to 50° C. for 4 h then concentrated in vacuo and the residue partitioned between water (100 ml) and dichloromethane (150 ml). The organic layer was separated, further washed with water (2×100 ml), dried over sodium sulphate and filtered through a silica gel pad. The resulting yellow solution was evaporated to dryness in vacuo to give ethyl 2-ethoxy-3-(3-nitrophenyl)acrylate as a yellow solid (5.6 g, 72%).

Step 4

A solution of potassium hydroxide (1.3 g, 22.2 mol) in water (20 ml) was added to a stirred solution of ethyl 2-ethoxy-3-(3-nitrophenyl)acrylate (5.6 g, 21.1 mmol) in methanol (100 ml) and the resulting mixture heated to reflux overnight. The methanol was then evaporated in vacuo and the residue diluted with water (150 ml). The solution was washed with dichloromethane (2×80 ml), filtered through a pad of celite and then acidified by the addition of 3M HCl to pH 3. The mixture was refrigerated for 18 h then the precipitated solid was collected by filtration, washed with water (3×30 ml) and dried in vacuo at 40° C. The resulting solid was recrystallized from ethyl acetate and heptane to give 2-ethoxy-3-(3-nitrophenyl)acrylic acid as a yellow solid (3.06 g, 61%).

$^1$H NMR (δ, 250 MHz, DMSO-$d_6$)=1.34 (3H, t, 7 Hz), 4.10 (2H, q, 7 Hz), 7.04 (1H, s), 7.69 (1H, t, 7.93 Hz), 8.07-8.22 (2H, m), 8.80 (1H, m), 13.25 (1H, brs).

Step 5

A mixture of 2-ethoxy-3-(3-nitrophenyl)acrylic acid (3.06 g, 12.9 mmol), methanol (150 ml) and 5% palladium on activated charcoal (0.60 g, 2 mol %) was hydrogenated at 12-30 psi $H_2$ atmosphere for 2 hr. The mixture was then filtered through celite, the filter cake washed with methanol and the filtrates concentrated at 40° C. under vacuum to give the product as a foamy solid. This was dissolved in water (100 ml) and the solution freeze-dried to give (±)-2-ethoxy-3-(3'-aminophenyl)-propanoic acid (2.7 g, 100%) as an off-white solid.

$^1$H NMR (δ, 250 MHz, DMSO-$d_6$)=1.07 (3H, t, 7 Hz), 2.6-2.85 (2H, m), 3.20-3.38 (1H, m), 3.40-3.60 (1H, m), 3.92 (1H, dd, 5 & 7.7 Hz), 6.3-6.45 (3H, m), 7.01 (1H, t, 7.6 Hz).

EXAMPLE 9

Molecular Modelling

Molecular modelling studies were performed using SYBYL software version 6.9.1 (Tripos Associates Inc, St Louis, Mo.) running on Silicon Graphics workstations. Three-dimensional model of the zwitterion form of 5-ASA was built from a standard fragments library, and its geometry was subsequently optimized using the Tripos force field (3) As the pKa of compounds are still unknown, the SPARC online calculator was used to determine the species occurring at physiological pH (7.4)(http://lbmlc2.chem.uga.edu/sparc/index.cfm). Three-dimensional model of ionized compounds were built from a standard fragments library, and their geometry was subsequently optimized using the Tripos force field (3) including the electrostatic term calculated from Gasteiger and Hückel atomic charges. The method of Powell available in Maximin2 procedure was used for energy minimization until the gradient value was smaller than 0.001 kcal/mol. Å.

The structure of the human PPARγ ligand-binding domain was obtained from its complexed X-Ray crystal structure with the tesaglitazar (AZ 242) available in the RCSB Protein Data Bank (1I7I) (4,5). Flexible docking of the compounds into the receptor active site was performed using GOLD software (6). The most stable docking models were selected according to the best scored conformation predicted by the GoldScore (6) and X-Score scoring functions (7). The complexes were energy-minimized using the Powell method available in Maximin2 procedure with the Tripos force field and a dielectric constant of 4.0 until the gradient value reached 0.01 kcal/mol. Å. The anneal function was used defining around the ligand a hot region (10 Å) and an interesting region (15 Å).

Results

The molecular modelling receptor docking studies predicted that, in general, the S enantiomer is more active that the R enantiomer, even though R enantiomer does show activity also. This phenomenon of one enantiomer being more biologically active is well known.

As a consequence, the present invention provides a method to resolve the compounds into enantiomers. The resolution method for compound 32 is shown schematically in FIG. 11.

While not wishing to be bound by theory, it is believed that the S-enantiomers of the compounds will afford higher activity. The results of the docking studies are shown in FIGS. 5-10.

EXAMPLE 7

Method of Preparing (±)-2-ethoxy 3-(4'-aminophenyl)-propionic Acid (Compound 39). Enantiomeric Resolution (FIG. 12A and FIG. 12B)

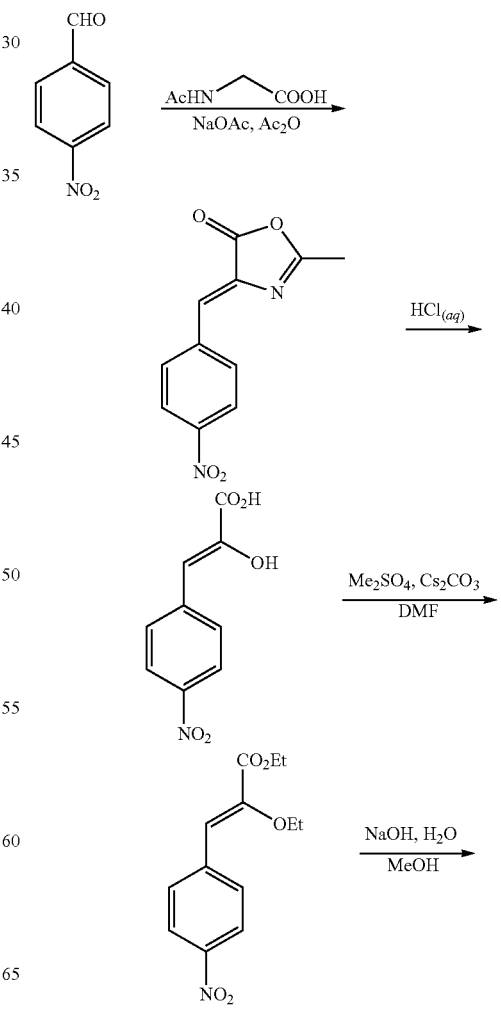

-continued

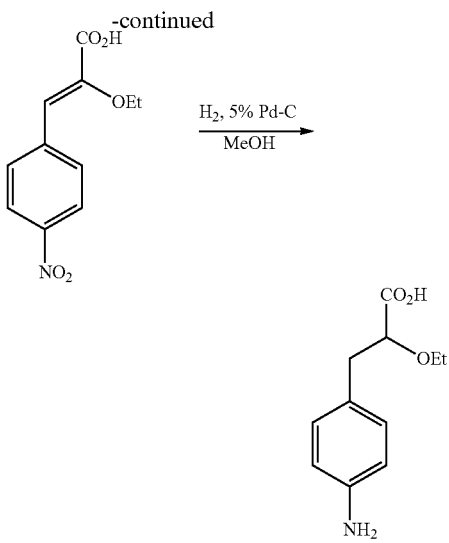

Steps 1 & 2
As per compound 34 steps 1 & 2.
Step 3
2-Hydroxy-3-(4-nitrophenyl)acrylic acid (20 g, 95.6 mmol) was suspended in DMF (200 ml). $Cs_2CO_3$ (74.9 g, 229.9 mmol) and diethyl sulphate (26.3 ml, 201 mmol) were added and dissolution was observed. After stirring for 18 hr at 18° C. water (350 ml) and ethyl acetate (250 ml) were added and the layers separated. The aqueous layer was further extracted with ethyl acetate (5×200 ml) then the combined organics were washed with water (2×200 ml), brine (2×200 ml) and dried over magnesium sulfate. The organics were concentrated to dryness to obtain ethyl 2-ethoxy-3-(4-nitrophenyl)-acrylate as an orange solid containing 3.6% by mass DMF (27.6 g wet, >100% yield). $^1$H NMR (δ, 250 MHz, DMSO-$d_6$): 1.32 (t, 6-H, 2×$CH_2CH_3$), 4.13 (q, 2-H, $CH_2CH_3$), 4.30 (q, 2-H, $CH_2CH_3$), 6.99 (s, 1-H, CH=), 8.06 (d, 2-H, CHaromatic), 8.26 (d, 2-H, CHaromatic).

Step 4
Ethyl 2-ethoxy-3-(4-nitrophenyl)acrylate containing 3.6 wt % DMF (26.07 g corrected, 98.3 mmol) was dissolved in IMS (500 ml) and a solution of NaOH (1.44 g, 36.1 mmol) in water (260 ml) was added. The resulting mixture was stirred at ambient temperature for 18 hr then acidified with 1M HCl (120 ml) and the resulting solid collected by filtration, washed with water (2×100 ml) and suction dried on the filter for 30 mins, followed by Results
Activation of PPARγ results in a cascade of reactions leading to a binding to specific DNA sequence elements termed peroxisome proliferator response elements (PPRE) (7-9).

We investigated PPARγ transcriptional activity by transient transfections of epithelial cells with the renilla luciferase and PPRE plasmids. To evaluate if the new molecules have more efficacy than 5-ASA to stimulate PPARγ activation, we tested these molecules at a concentration of 1 mM. Effect of the new molecules at a concentration of 1 mM was compared to 5-ASA and rosiglitazone, used as positive controls at optimal concentrations of 30 mM and $10^{-5}$ M respectively. Cells were stimulated with the different molecules during 24 hours.

Analysis of PPARγ activity in transfected HT-29 cells showed that the new molecules 34, 39, 35 and 40 at 1 mM increased the reporter gene activity by 4.8±0.71; 2.73±0.31; 2.64±0.46: 3.4±0.97 fold respectively, thereby displaying an activity similar or superior to 5-ASA at 30 mM (2.8±0.7) and rosiglitazone at $10^{-5}$ M (3.17±0.29).

FIG. 2 represents all the results obtained for each molecule assessed in 2 or 3 experiments done in triplicate. Reproducibility between the different experiments is good and similar to data described in the literature.

This study allowed us to identify 4 new molecules having 30 to 50 times more efficacy than 5-ASA to activate PPARγ.

EXAMPLE 11

Colon Cancer Cell Growth
The following substances (i.e. 20, 34, 35, 39 and 40) were tested for their ability to modulate colon cancer cell growth. For this purpose, three human colon carcinoma cell lines (i.e. HT-29, HT-115 and DLD-1) were used. These cell types were selected on the basis of the cyclooxigenase-2 (COX-2) expression. Indeed, HT-115 cells express a biologically active COX-2, HT-29 cells express a non-functional COX-2 isoform, and DLD-1 are COX-2-deficient cells. It is believed that these molecules are also active on cells that do not express COX-, and thus the molecules of the present invention may be used in cells which do not express COX-2 for the purposes of treating tumours and other applications as herein described.

HT-29 and DLD-1 cells were cultured in McCoy and RPMI1640 media respectively, supplemented with 10% fetal bovine serum (FBS), 1% penicillin/streptomycin (P/S) and 50 mg/ml gentamycin. HT-115 were cultured in DMEM medium supplemented with 15% FBS and 1% P/S. Cells were maintained in a humidified incubator at 37° C., in the presence of 5% CO2.

For cell growth assays, single-cell suspensions were plated at 2×103 cells/well (4×103 cells/well for HT115) in 96-well culture dishes in medium containing 0.5% FBS and allowed to adhere. The non-adherent cells were then removed, and fresh medium containing 0.5% FBS was added into each well. Cells were cultured in the presence or absence of the specified substances. Each substance was dissolved as a 25 mM stock solution in culture medium containing 0.5% FBS, and the pH of each stock solution was adjusted to 7.4, if necessary, with NaOH. Substances were used at a final concentration ranging from 0.5 to 10 mM.

Cell proliferation was determined by measuring the incorporation of 5-bromo-2'-deoxyuridine (BrdU) into DNA using a commercially available cell proliferation kit (Roche Diagnostics, Monza, Italy). BrdU was added to the cell cultures during the last 6 hours of incubation, and the level of BrdU-positive cells was assessed after 48 h culture by enzyme-linked immunosorbent assay (ELISA), Optical density (OD) was determined at 450 nm using an ELISA reader. Experiments were performed in triplicate and the results are reported as the mean±standard deviation (SD).

Results
The compounds differed in their ability to inhibit colon cancer cell growth. Results are summarized in Table 1 where the percentage of inhibition of growth of DLD-1 cells by the specified compounds is shown. The substance 20, exhibits a marked anti-proliferative effect in a dose-dependent fashion, in each of the three cell lines tested (FIG. 3 and FIG. 4). More than 90% of cell growth Inhibition was seen when compounds were used at a final concentration of 10 mM. The ability of the compound 20 to significantly inhibit cell growth was seen when used at a final concentration of 5 or 10 mM.

The compounds 34 and 39 slightly reduced the cell growth when used at high doses (10 mM) (FIG. 4), but differences among groups were not statistically significant. Similarly, no inhibition in cell growth was seen in cultures added with the substances 35, and 40 (see Table 1).

CONCLUSIONS

This first set of examples of the invention (Example 10) shows the ability of four optimized molecules 34, 39, 35 and 40 at concentration of 1 mM, to increase the PPARγ activity in transfected HT-29 cells, displaying an activity similar or superior to 5-ASA at 30 mM and rosiglitazone at $10^{-5}$ M.

The second set examples of the invention (Example 11) shows that the compounds affect the inhibition of the growth of the colon cancer cell lines, HT-29, HT-115 and DLD1 to varying degrees. The compounds differed in their ability to inhibit colon cancer cell growth. The substance 20, exhibits a marked anti-proliferative effect on cell lines tested.

These molecules of the present invention are also active on cells that do not express COX-2, and thus the molecules of the present invention may be used in cells which do not express COX-2 for the purposes of treating tumours and other applications as herein described.

OVERALL CONCLUSIONS

The synthesized highest ranking compounds, indicated from modelling studies, all show an activity similar/superior to that of mesalazine.

REFERENCES

1. Dubuquoy, L., E. A. Jansson, S. Deeb, S. Rakotobe, M. Karoui, J. F. Colombel, J. Auwerx, S. Petterason, and P. Desreumaux, 2003. Impaired expression of peroxisome proliferator-activated receptor gamma in ulcerative colitis. *Gastroenterology* 124:1265-1276.
2. Rousseaux C, Lefebvre B, Dubuquoy L, Lefebvre P, Romano O, Auwerx J, Metzger D, Wahii W, Desvergne B. Naccari G C, Chavatte P, Farce A, Bulois P, Cortot A, Colombel J F, Desreumaux P. Intestinal anti-inflammatory effect of 5-amino salicylic acid is dependent on PPARγ. *J Exp Med* 2005; 201: 1205-15.
3. Clark, M. C. R. D. I. V. O., N, 1989. Validation of the General Purpose Tripos 5.2 Field. *J. Comput Chem.* 10:982-1012.
4. Gampe, R. T., Jr., V. G. Montana, M. H. Lambert, A. B. Miller, R. K. Bledsoe, M. V. Milburn, S. A. Kliewer, T. M. Willson, and H. E. Xu, 2000. Asymmetry in the PPARγ/RXRalpha crystal structure reveals the molecular basis of heterodimerization among nuclear receptors. *Mol Cell* 5:545-555.
5. Jones, G., P. Willett, R. C. Glen, A. R. Leach, and R. Taylor, 1997. Development and validation of a genetic algorithm for flexible docking. *J Mol Biol* 267:727-748.
6. Wang, R., L. Lai, and S. Wang, 2002. Further development and validation of empirical scoring functions for structure-based binding affinity prediction. *J Comput Aided Mol Des* 16:11-26.
7. Westin, S., R, Kurokawa, R. T. Nolte, G. B. Wisely, E. M. McInerney. D. W. Rose, M. V. Milburn, M. G. Rosenfeld, and C. K. Glass, 1998. Interactions controlling the assembly of nuclear-receptor heterodimers and co-activators. *Nature* 395:199-202.
8. Mangelsdorf, D. J., C. Thummel, M. Beato, P. Herrlich, G. Schutz, K. Umesono, B. Blumberg, P. Kastner, M. Mark, P. Chambon, and et al. 1995. The nuclear receptor superfamily: the second decade. *Cell* 83:835-839.
9. Misra, P., E. D. Owuor, W. Li, S. Yu, C. Qi, K. Meyer, Y. J. Zhu, M. S. Rao, A. N. Kong, and J. K. Reddy, 2002. Phosphorylation of transcriptional coactivator peroxisome proliferator-activated receptor (PPAR)-binding protein (PBP). Stimulation of transcriptional regulation by mitogen-activated protein kinase. *J Biol Chem* 277: 48745-48754. Epub 422 Sep 48727.

The invention claimed is:
1. A method of treating ulcerative rectocolitis in a mammal in need thereof, the method comprising administering to the mammal a compound represented by:

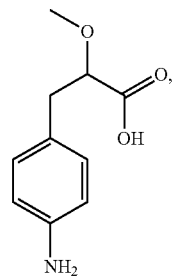

or a pharmaceutically acceptable salt or a stereoisomer thereof.
2. The method of claim 1, wherein the mammal is a human.
3. The method of claim 1, wherein the compound is (R)-2-methoxy-3-(4'-aminophenyl)propionic acid.
4. The method of claim 1, wherein the compound is (S)-2-methoxy-3-(4'-aminophenyl)propionic acid.
5. The method of claim 1, wherein the compound is in an enantiomerically pure R form.
6. The method of claim 1, wherein the compound is in an enantiomerically pure S form.
7. A method of treating ulcerative rectocolitis in a mammal in need thereof, the method comprising administering to the mammal a pharmaceutical composition comprising:
   a compound represented by:

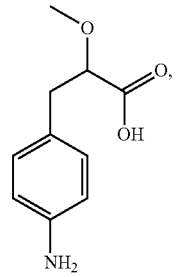

or a pharmaceutically acceptable salt or a stereoisomer thereof; and
   a pharmaceutically acceptable excipient.
8. The method of claim 7, wherein the mammal is a human.
9. The method of claim 7, wherein the compound is (R)-2-methoxy-3-(4'-aminophenyl)propionic acid.
10. The method of claim 7, wherein the compound is (S)-2-methoxy-3-(4'-aminophenyl)propionic acid.

11. The method of claim 7, wherein the compound is in an enantiomerically pure R form.

12. The method of claim 7, wherein the compound is in an enantiomerically pure S form.

* * * * *